United States Patent
Kyle et al.

(10) Patent No.: US 11,246,714 B2
(45) Date of Patent: Feb. 15, 2022

(54) SURGICAL INSTRUMENT FOR IMPLANTING A SEMI-RIGID MEDICAL IMPLANT

(71) Applicant: SAG, LLC, Excelsior, MN (US)

(72) Inventors: Matthew Kyle, Minnetonka, MN (US); Jeffrey C. Felt, Minnetonka, MN (US); Mark A. Rydell, Minnetonka, MN (US); Stephen H. Crosbie, Minnetonka, MN (US); John P. Mehawej, Minnetonka, MN (US)

(73) Assignee: SAG, LLC, Excelsior, MN (US)

( * ) Notice: Subject to any disclaimer, the term of this patent is extended or adjusted under 35 U.S.C. 154(b) by 42 days.

(21) Appl. No.: 16/366,919

(22) Filed: Mar. 27, 2019

(65) Prior Publication Data

US 2019/0282375 A1    Sep. 19, 2019

Related U.S. Application Data

(63) Continuation-in-part of application No. 15/363,295, filed on Nov. 29, 2016, now abandoned, which is a
(Continued)

(51) Int. Cl.
*A61F 2/44*   (2006.01)
*A61F 2/46*   (2006.01)
*A61F 2/30*   (2006.01)

(52) U.S. Cl.
CPC .......... *A61F 2/4425* (2013.01); *A61F 2/442* (2013.01); *A61F 2/4611* (2013.01);
(Continued)

(58) Field of Classification Search
CPC ............ A61F 2/4425; A61F 2002/4435; A61F 2002/448; A61F 2002/4485
(Continued)

(56) References Cited

U.S. PATENT DOCUMENTS

| 3,030,951 A | 4/1962 | Mandarino |
| 3,728,742 A | 4/1973 | Averill et al. |

(Continued)

FOREIGN PATENT DOCUMENTS

| CN | 101193608 A | 6/2008 |
| CN | 106073953 A | 11/2016 |

(Continued)

OTHER PUBLICATIONS

An et al., "The Future of Spinal Fuzion. Txt." Ortho SuperSite, Aug. 2006 pp. 1-3.
(Continued)

*Primary Examiner* — Matthew J Lawson
(74) *Attorney, Agent, or Firm* — Michael A. Bondi; Moss & Barnett

(57) ABSTRACT

A surgical instrument for implanting a semi-rigid medical implant. The surgical instrument includes a shaft, an accessory shaft, an actuation mechanism and an implant engagement mechanism. The shaft has a channel formed therein. The shaft has a proximal end and a distal end. The accessory shaft is slidably mounted in the channel. The accessory shaft has a proximal end and a distal end. The actuation mechanism is mounted to the shaft proximate the proximal end thereof. The actuation mechanism is capable of causing the accessory shaft to slide with respect to the shaft. The implant engagement mechanism is attached to the distal end of the accessory shaft. The implant engagement mechanism is capable of engaging a semi-rigid surgical implant.

18 Claims, 25 Drawing Sheets

Related U.S. Application Data continuation of application No. 13/833,998, filed on Mar. 15, 2013, now Pat. No. 9,510,953.

(60) Provisional application No. 61/685,383, filed on Mar. 16, 2012.

(52) U.S. Cl.
CPC ............... *A61F 2002/305* (2013.01); *A61F 2002/30069* (2013.01); *A61F 2002/30331* (2013.01); *A61F 2002/30367* (2013.01); *A61F 2002/30387* (2013.01); *A61F 2002/30604* (2013.01); *A61F 2002/444* (2013.01); *A61F 2002/4687* (2013.01)

(58) Field of Classification Search
USPC .............................. 623/17.11–17.16; 289/1.5
See application file for complete search history.

(56) References Cited

U.S. PATENT DOCUMENTS

| | | |
|---|---|---|
| 3,815,599 A | 6/1974 | Deyerle |
| 3,848,601 A | 11/1974 | Ma et al. |
| 3,867,728 A | 2/1975 | Stubstad et al. |
| 3,867,729 A | 2/1975 | Stubstad et al. |
| 4,081,866 A | 4/1978 | Upshaw et al. |
| 4,203,444 A | 5/1980 | Bonnell et al. |
| 4,349,921 A | 9/1982 | Kuntz |
| 4,456,745 A | 6/1984 | Rajan |
| 4,463,141 A | 7/1984 | Robinson |
| 4,476,293 A | 10/1984 | Robinson |
| 4,477,604 A | 10/1984 | Oechsle, III |
| 4,502,161 A | 3/1985 | Wall |
| 4,647,643 A | 3/1987 | Zdrahala et al. |
| 4,651,736 A | 3/1987 | Sanders |
| 4,711,639 A | 12/1987 | Grundei |
| 4,722,948 A | 2/1988 | Sanderson |
| 4,743,256 A | 5/1988 | Brantigan |
| 4,743,632 A | 5/1988 | Marinovic |
| 4,772,287 A | 9/1988 | Ray et al. |
| 4,808,691 A | 2/1989 | Konig et al. |
| 4,834,757 A | 5/1989 | Brantigan |
| 4,863,476 A | 9/1989 | Shepperd |
| 4,873,308 A | 10/1989 | Coury et al. |
| 4,880,610 A | 11/1989 | Constantz |
| 4,904,260 A | 2/1990 | Ray et al. |
| 4,911,718 A | 3/1990 | Lee et al. |
| 4,969,888 A | 11/1990 | Scholten et al. |
| 5,007,940 A | 4/1991 | Berg |
| 5,047,055 A | 9/1991 | Bao et al. |
| 5,067,964 A | 11/1991 | Richmond et al. |
| 5,082,803 A | 1/1992 | Sumita |
| 5,108,404 A | 4/1992 | Scholten et al. |
| 5,109,077 A | 4/1992 | Wick |
| 5,143,942 A | 9/1992 | Brown |
| 5,166,115 A | 11/1992 | Brown |
| 5,192,326 A | 3/1993 | Bao et al. |
| 5,192,327 A | 3/1993 | Brantigan |
| 5,254,662 A | 10/1993 | Szycher et al. |
| 5,263,987 A | 11/1993 | Shah |
| 5,278,201 A | 1/1994 | Dunn et al. |
| 5,344,458 A | 9/1994 | Bonutti |
| 5,344,459 A | 9/1994 | Swartz |
| 5,397,364 A | 3/1995 | Kozak et al. |
| 5,458,643 A | 10/1995 | Oka et al. |
| 5,496,323 A | 3/1996 | Dye |
| 5,509,934 A | 4/1996 | Cohen |
| 5,514,180 A | 5/1996 | Heggeness |
| 5,522,899 A | 6/1996 | Michelson |
| 5,525,418 A | 6/1996 | Hashimoto et al. |
| 5,545,229 A | 8/1996 | Parsons et al. |
| 5,549,683 A | 8/1996 | Bonutti |
| 5,554,191 A | 9/1996 | Lahille et al. |
| 5,556,429 A | 9/1996 | Felt |
| 5,562,736 A | 10/1996 | Ray et al. |
| 5,609,635 A | 3/1997 | Michelson |
| 5,624,463 A | 4/1997 | Stone et al. |
| 5,674,294 A | 10/1997 | Bainville et al. |
| 5,702,453 A | 12/1997 | Rabbe et al. |
| 5,702,454 A | 12/1997 | Baumgartner |
| 5,725,531 A | 3/1998 | Shapiro |
| 5,755,797 A | 5/1998 | Baumgartner |
| 5,772,661 A | 6/1998 | Michelson |
| 5,776,199 A | 7/1998 | Michelson |
| 5,795,353 A | 8/1998 | Felt |
| 5,800,547 A | 9/1998 | Schafer et al. |
| 5,824,093 A | 10/1998 | Ray et al. |
| 5,860,973 A | 1/1999 | Michelson |
| 5,861,041 A | 1/1999 | Tienboon et al. |
| 5,888,220 A | 3/1999 | Felt et al. |
| 5,888,227 A | 3/1999 | Cottle |
| 5,888,228 A | 3/1999 | Knothe et al. |
| 5,893,889 A | 4/1999 | Harringson |
| 5,919,236 A | 7/1999 | Pfaff et al. |
| 5,944,759 A | 8/1999 | Link |
| 5,980,522 A | 11/1999 | Koros et al. |
| 5,989,289 A | 11/1999 | Coates et al. |
| 5,989,291 A | 11/1999 | Ralph et al. |
| 6,033,438 A | 3/2000 | Bianchi et al. |
| 6,048,345 A | 4/2000 | Berke et al. |
| 6,079,868 A | 6/2000 | Rydell |
| 6,080,193 A | 6/2000 | Hochshuler et al. |
| 6,096,038 A | 8/2000 | Michelson |
| 6,096,080 A | 8/2000 | Nicholson et al. |
| 6,102,950 A | 8/2000 | Vaccaro |
| 6,110,210 A | 8/2000 | Norton et al. |
| 6,113,638 A | 9/2000 | Williams et al. |
| 6,117,174 A | 9/2000 | Nolan |
| 6,132,472 A | 10/2000 | Bonutti |
| 6,139,579 A | 10/2000 | Steffee et al. |
| 6,140,452 A | 10/2000 | Felt et al. |
| 6,143,033 A | 11/2000 | Paul et al. |
| 6,146,422 A | 11/2000 | Lawson |
| 6,159,211 A | 12/2000 | Boriani et al. |
| 6,174,311 B1 | 1/2001 | Branch et al. |
| 6,176,882 B1 | 1/2001 | Bledermann et al. |
| 6,183,517 B1 | 2/2001 | Suddaby |
| 6,190,414 B1 | 2/2001 | Young et al. |
| 6,206,923 B1 | 3/2001 | Boyd et al. |
| 6,206,927 B1 | 3/2001 | Fell et al. |
| 6,224,630 B1 | 5/2001 | Bao et al. |
| 6,224,631 B1 | 5/2001 | Kohrs |
| 6,245,108 B1 | 6/2001 | Biscup |
| 6,248,131 B1 | 6/2001 | Felt et al. |
| 6,251,140 B1 | 6/2001 | Marino et al. |
| 6,258,125 B1 | 7/2001 | Paul et al. |
| 6,264,695 B1 | 7/2001 | Stoy |
| 6,270,528 B1 | 8/2001 | McKay |
| 6,302,914 B1 | 10/2001 | Michelson |
| 6,342,075 B1 | 1/2002 | MacArthur |
| 6,348,071 B1 | 2/2002 | Steffee et al. |
| 6,371,988 B1 | 4/2002 | Pafford et al. |
| 6,371,990 B1 | 4/2002 | Ferree |
| 6,387,130 B1 | 5/2002 | Stone et al. |
| 6,419,704 B1 | 7/2002 | Ferree |
| 6,419,705 B1 | 7/2002 | Erickson |
| 6,436,140 B1 | 8/2002 | Liu et al. |
| 6,436,143 B1 | 8/2002 | Ross et al. |
| 6,440,169 B1 | 8/2002 | Elberg et al. |
| 6,443,988 B2 | 9/2002 | Felt et al. |
| 6,468,311 B2 | 10/2002 | Boyd et al. |
| 6,488,710 B2 | 12/2002 | Besselink |
| 6,511,509 B1 | 1/2003 | Ford et al. |
| 6,524,341 B2 | 2/2003 | Lang et al. |
| 6,533,818 B1 | 3/2003 | Weber et al. |
| 6,537,280 B2 | 3/2003 | Dinger et al. |
| 6,558,421 B1 | 5/2003 | Fell et al. |
| 6,558,424 B2 | 5/2003 | Thalgott |
| 6,562,074 B2 | 5/2003 | Gerbec et al. |
| 6,595,998 B2 | 7/2003 | Johnson et al. |
| 6,610,092 B2 | 8/2003 | Ralph et al. |
| 6,610,093 B1 | 8/2003 | Pisharodi |
| 6,620,196 B1 | 9/2003 | Trieu |

(56) References Cited

U.S. PATENT DOCUMENTS

| | | |
|---|---|---|
| 6,648,917 B2 | 11/2003 | Gerbec et al. |
| 6,652,587 B2 | 11/2003 | Felt et al. |
| 6,669,732 B2 | 12/2003 | Serhan et al. |
| 6,726,720 B2 | 4/2004 | Ross et al. |
| 6,726,721 B2 | 4/2004 | Stoy et al. |
| 6,733,535 B2 | 5/2004 | Michelson |
| 6,740,093 B2 | 5/2004 | Hochschuler et al. |
| 6,746,454 B2 | 6/2004 | Winterbottom |
| 6,764,514 B1 | 7/2004 | Li et al. |
| 6,770,095 B2 | 8/2004 | Grinberg et al. |
| 6,773,460 B2 | 8/2004 | Jackson |
| 6,793,678 B2 | 9/2004 | Hawkins |
| 6,821,298 B1 | 11/2004 | Jackson |
| 6,830,574 B2 | 12/2004 | Heckele |
| 6,835,206 B2 | 12/2004 | Jackson |
| 6,852,129 B2 | 2/2005 | Gerbec et al. |
| 6,855,165 B2 | 2/2005 | Fell et al. |
| 6,855,167 B2 | 2/2005 | Shimp et al. |
| 6,866,684 B2 | 3/2005 | Fell et al. |
| 6,893,463 B2 | 5/2005 | Fell et al. |
| 6,896,701 B2 | 5/2005 | Boyd et al. |
| 6,911,044 B2 | 6/2005 | Fell et al. |
| 6,923,831 B2 | 8/2005 | Fell et al. |
| 6,966,928 B2 | 11/2005 | Fell et al. |
| 7,001,431 B2 | 2/2006 | Bao et al. |
| 7,008,452 B2 | 3/2006 | Hawkins |
| 7,018,416 B2 | 3/2006 | Hanson et al. |
| 7,097,663 B1 | 8/2006 | Nicol |
| 7,238,204 B2 | 7/2007 | Le Couedic et al. |
| 7,267,690 B2 | 9/2007 | Felt |
| 7,291,171 B2 | 11/2007 | Ferree |
| 7,297,161 B2 | 11/2007 | Fell |
| 7,320,709 B2 | 1/2008 | Felt et al. |
| 7,341,602 B2 | 3/2008 | Fell et al. |
| 7,392,089 B2 | 6/2008 | Wahlstrand |
| 7,491,235 B2 | 2/2009 | Fell |
| 7,491,237 B2 | 2/2009 | Randall et al. |
| 7,549,995 B2 | 6/2009 | Schultz |
| 7,563,285 B2 | 7/2009 | Ralph et al. |
| 7,591,853 B2 | 9/2009 | Felt et al. |
| 7,618,458 B2 | 11/2009 | Biedermann et al. |
| 7,621,960 B2 | 11/2009 | Boyd et al. |
| 7,666,228 B2 | 2/2010 | Le Couedic et al. |
| 7,914,582 B2 | 3/2011 | Felt et al. |
| 8,038,718 B2 | 10/2011 | Palm et al. |
| 8,080,004 B2 | 12/2011 | Downey |
| 8,100,977 B2 | 1/2012 | Felt |
| 8,100,979 B2 | 1/2012 | Felt |
| 8,172,902 B2 | 5/2012 | Kapitan |
| 8,196,796 B2 | 6/2012 | Shelton, IV |
| 8,828,019 B1 | 9/2014 | Raymond et al. |
| 9,186,143 B2 | 11/2015 | Timm |
| 9,510,953 B2 | 12/2016 | Felt et al. |
| 9,737,414 B2 | 8/2017 | Felt |
| 10,195,048 B2 | 2/2019 | Felt |
| 2001/0004710 A1 | 6/2001 | Felt et al. |
| 2001/0047207 A1 | 11/2001 | Michelson |
| 2002/0026244 A1 | 2/2002 | Trieu |
| 2002/0029084 A1 | 3/2002 | Paul et al. |
| 2002/0099444 A1 | 7/2002 | Boyd et al. |
| 2002/0127264 A1 | 9/2002 | Felt et al. |
| 2002/0128713 A1 | 9/2002 | Ferree |
| 2002/0183850 A1 | 12/2002 | Felt et al. |
| 2003/0055506 A1 | 3/2003 | Stoy et al. |
| 2003/0065396 A1 | 4/2003 | Michelson |
| 2003/0109928 A1 | 6/2003 | Pasquet |
| 2003/0125739 A1 | 7/2003 | Bagga et al. |
| 2003/0130739 A1 | 7/2003 | Gerbec et al. |
| 2003/0135279 A1 | 7/2003 | Michelson |
| 2003/0220691 A1 | 11/2003 | Songer et al. |
| 2003/0230198 A1 | 12/2003 | Zitttel |
| 2003/0236571 A1 | 12/2003 | Ralph et al. |
| 2004/0002761 A1 | 1/2004 | Rogers et al. |
| 2004/0006393 A1 | 1/2004 | Burkinshaw |
| 2004/0010318 A1 | 1/2004 | Ferree |
| 2004/0019354 A1 | 1/2004 | Johnson et al. |
| 2004/0054413 A1 | 3/2004 | Higham et al. |
| 2004/0059421 A1 | 3/2004 | Glenn et al. |
| 2004/0064144 A1 | 4/2004 | Johnson et al. |
| 2004/0111155 A1 | 6/2004 | Ferree |
| 2004/0127994 A1 | 7/2004 | Kast et al. |
| 2004/0162618 A1 | 8/2004 | Mujwid et al. |
| 2004/0172134 A1 | 9/2004 | Berry |
| 2004/0186576 A1 | 9/2004 | Biscup et al. |
| 2004/0220580 A1 | 11/2004 | Johnson et al. |
| 2004/0220672 A1 | 11/2004 | Shadduck |
| 2004/0225363 A1 | 11/2004 | Richelsoph |
| 2004/0230198 A1 | 11/2004 | Manzi et al. |
| 2004/0267366 A1 | 12/2004 | Kruger |
| 2004/0267367 A1 | 12/2004 | O'Neil |
| 2005/0010290 A1 | 1/2005 | Hawkins |
| 2005/0010295 A1 | 1/2005 | Michelson |
| 2005/0015150 A1 | 1/2005 | Lee |
| 2005/0033424 A1 | 2/2005 | Fell |
| 2005/0055097 A1 | 3/2005 | Grunberg et al. |
| 2005/0131543 A1 | 6/2005 | Benzel et al. |
| 2005/0154463 A1 | 7/2005 | Trieu |
| 2005/0154465 A1 | 7/2005 | Trieu |
| 2005/0187633 A1 | 8/2005 | Ferree |
| 2005/0203599 A1 | 9/2005 | Garabedian et al. |
| 2005/0228500 A1 | 10/2005 | Kim et al. |
| 2005/0234555 A1 | 10/2005 | Sutton et al. |
| 2005/0240267 A1 | 10/2005 | Randall et al. |
| 2005/0273178 A1 | 12/2005 | Boyan et al. |
| 2006/0004454 A1 | 1/2006 | Ferree et al. |
| 2006/0025861 A1 | 2/2006 | McKay |
| 2006/0058807 A1 | 3/2006 | Landry et al. |
| 2006/0058880 A1 | 3/2006 | Wysocki et al. |
| 2006/0069438 A1 | 3/2006 | Zucherman et al. |
| 2006/0106462 A1 | 5/2006 | Tsou |
| 2006/0142858 A1 | 6/2006 | Colleran et al. |
| 2006/0142862 A1 | 6/2006 | Diaz et al. |
| 2006/0149383 A1 | 7/2006 | Arnin et al. |
| 2006/0167550 A1 | 7/2006 | Snell et al. |
| 2006/0173542 A1 | 8/2006 | Shikinami |
| 2006/0178745 A1 | 8/2006 | Bartish et al. |
| 2006/0189999 A1 | 8/2006 | Zwirkoski |
| 2006/0190083 A1 | 8/2006 | Arnin et al. |
| 2006/0195191 A1 | 8/2006 | Sweeney et al. |
| 2006/0212118 A1 | 9/2006 | Abernathie |
| 2006/0235535 A1 | 10/2006 | Ferree et al. |
| 2006/0247778 A1* | 11/2006 | Ferree ............... A61F 2/442 623/17.14 |
| 2006/0247781 A1 | 11/2006 | Francis |
| 2006/0259144 A1 | 11/2006 | Trieu |
| 2006/0264965 A1 | 11/2006 | Shadduck et al. |
| 2006/0293756 A1* | 12/2006 | Felt ............... A61F 2/4611 623/17.16 |
| 2007/0027546 A1 | 2/2007 | Palm |
| 2007/0032874 A1 | 2/2007 | Lee et al. |
| 2007/0050036 A1 | 3/2007 | Felt |
| 2007/0233255 A1 | 10/2007 | Song et al. |
| 2007/0244485 A1 | 10/2007 | Greenhalgh et al. |
| 2008/0039942 A1 | 2/2008 | Bergeron |
| 2008/0065220 A1 | 3/2008 | Alleyne et al. |
| 2008/0119853 A1 | 5/2008 | Felt et al. |
| 2008/0133017 A1* | 6/2008 | Beyar ............... A61F 2/4611 623/17.16 |
| 2008/0140206 A1* | 6/2008 | Felt ............... A61F 2/4611 623/17.16 |
| 2008/0208343 A1 | 8/2008 | Felt |
| 2008/0234820 A1 | 9/2008 | Felt et al. |
| 2008/0249622 A1* | 10/2008 | Gray ............... A61F 2/4455 606/86 A |
| 2008/0262622 A1 | 10/2008 | Butler |
| 2009/0069895 A1 | 3/2009 | Gittings et al. |
| 2009/0138086 A1* | 5/2009 | Dewey ............... A61F 2/44 623/17.16 |
| 2009/0276047 A1 | 11/2009 | Felt et al. |
| 2010/0030338 A1 | 2/2010 | Simon |
| 2010/0057144 A1 | 3/2010 | Felt et al. |
| 2010/0145457 A1 | 6/2010 | Felt et al. |

(56) References Cited

U.S. PATENT DOCUMENTS

| | | |
|---|---|---|
| 2011/0270399 A1 | 11/2011 | Yurek et al. |
| 2012/0245689 A1 | 9/2012 | Gimbel |
| 2014/0277479 A1 | 9/2014 | Raymond |

FOREIGN PATENT DOCUMENTS

| | | |
|---|---|---|
| DE | 4339895 C1 | 3/1995 |
| DE | 19823325 C1 | 3/2000 |
| EP | 0353936 A1 | 2/1990 |
| EP | 0378002 A1 | 7/1990 |
| EP | 0505634 A1 | 9/1992 |
| EP | 0521573 A2 | 1/1993 |
| EP | 1752116 A1 | 2/2007 |
| FR | 2639823 A1 | 6/1990 |
| FR | 2781998 A1 | 2/2000 |
| WO | 1998/020939 A1 | 5/1988 |
| WO | 1993/011723 A1 | 6/1993 |
| WO | 1995/030388 A1 | 11/1995 |
| WO | 1995/031948 A1 | 11/1995 |
| WO | 1995031946 A1 | 11/1995 |
| WO | 1997/026847 A1 | 7/1997 |
| WO | 1999/044509 A1 | 9/1999 |
| WO | 1999/056800 A1 | 11/1999 |
| WO | 1999/061084 A1 | 12/1999 |
| WO | 2000/013619 A1 | 3/2000 |
| WO | 2000/059411 A1 | 10/2000 |
| WO | 2001/0066021 A1 | 9/2001 |
| WO | 2002/017821 A1 | 3/2002 |
| WO | 2003/099171 A1 | 12/2003 |
| WO | 2004/098466 A1 | 11/2004 |
| WO | 2005/051246 A1 | 6/2005 |
| WO | 2006/051547 A1 | 5/2006 |
| WO | 2006/127848 A2 | 11/2006 |
| WO | 2006/127849 A2 | 11/2006 |

OTHER PUBLICATIONS

Andersson et al., "Macintosh Arthroplasty in Rheumatoid Arthritis," Department of Orthopaedic Surgery and Department of Rheumatology, The London Hospital, London, England, 1974, pp. 245-259.

Cameron et al., "Review of a Failed Knee Replacement and Some Observations on the Design of a Knee Resurfacing Prosthesis," Archives of Orthopaedic and Traumatic Surgery, vol. 97, No. 1, 1980, pp. 87-89.

Clary et al., "Experience with the MacIntosh Knee Prosthesis," Southern Medical Journal, Journal of the Southern Medical Association, Mar. 1972, vol. 65, No. 3, pp. 265-272.

Cluett, "Discetomy—Spinal Surgery to remove herniated disc", Nov. 29, 2005. 3 pages, http://orthopedica.about.com/cs/herniateddisk/a/repturedisk 3.htm.

Conaty, "Surgery of the Hip and Knee in Patients with Rheumatoid Arthritis," The Arthritis Service (surgery) of Rancho, Los Amigos Hospital, Downey, Mar. 1973, vol. 55-A, No. 2, pp. 301-314.

Emerson et al., "The Use of the McKeever metallic Hemiarthroplasty for Unicompartmental Arthritis," The Journal of Bone and Joint Surgery, 1985, pp. 208-212.

Hackenberg et al., "Transforaminal lumbar interbody fusion: a safe technique with satisfactory three to five year results," Eur Spine J, 2005, pp. 551-558.

Hastings, "Double Hemiarthroplasty of the Knee in Rheumatoid Arthritis," The Journal of Bone and Joint Surgery, Feb. 1973, vol. 55 B, No. 1, pp. 112-118.

Jessop et al., "Follow-up of the Macintosh Arthroplasty of the Knee Joint," Rheum. Phys. Med., 1972, vol. XI, No. 5, pp. 224.

Kay et al., "The Macintosh Tibial Plateau Hemiprosthesis for the Rheumatoid Knee," The Journal of Bone and Joint Surgery, May 1972, vol. 54B, No. 2, pp. 256-262.

Kowalski et al., "Biomechanics of bone fusion," Neurosurg. Focus, Apr. 2001, vol. 10, pp. 1-7.

Kozinn et al., "Surgical Treatment of Unicompartmental Degenerative Arthritis of the Knee," Rheumatic Disease Clinics of North America, Dec. 1988, vol. 14, No. 3, pp. 545-564.

MacIntosh et al., "The Use of the Hemiarthroplasty Prosthesis for Advanced Osteoarthritis and Rheumatoid Arthritis of the Knee," The Journal of Bone and Joint Surgery, May 1972, vol. 54 B, No. 2, pp. 244-255.

McCallum et al., "Duplication of Medial Erosion in Unicompartmental Knee Arthroplasties," The Journal of Bone and Joint Surgery, 1995, pp. 726-728.

McCollum et al., "Tibial Plateau Prosthesis in Arthroplasty of the Knee," The Journal of Bone and Joint Surgery, Jun. 1970, vol. 52-A., No. 4, pp. 827828.

McKeever, "Tibial Plateau Prosthesis," The Classic, pp. 3-12. Jan.-Feb. 1985.

Norton, "I:300 Interbody Fusion Device Technology Analysis," ABS Advanced Biosurfaces, Inc., Mar. 26, 2007, pp. 1-18.

Porter, "MacIntosh Athroplasty: a long-term review," J.R. Coll. Surg. Edinb., Aug. 1988, vol. 33, pp. 199-201.

Potter, "Arthroplasty of the Knee in Rheumatoid Arthritis and Osteoarthritis," The Journal of Bone and Joint Surgery, Jan. 1972, vol. 54A, No. 1, pp. 1-24.

Potter, "Arthroplasty of the Knee with Tibial Metallic Implants of the McKeever and MacIntosh Design," Surgical Clinics of North America, Aug. 1969, vol. 49, No. 4, pp. 903-915.

Powers et al., "Minimally Invasive Fusion and Fixation Techniques," Neurosurg. Clinics of North America, 2006, pp. 477-489.

RSB Spine, LLC, "510(k) Summary," Sep. 18, 2007, 4 pages, Cleveland, Ohio.

Ryortho, "Here comes ProDisc" Orthopedics This Week, vol. 2, Issue 3. (published prior to Jan. 19, 2006).

Sbarbaro, "Hemitibial plateau prosthesis ten years' experience in 500 knee arthroplasties," Acta Orthopaedica Belgica, 1973, pp. 91-100.

Schorn et al., "MacIntosh Arthroplasty in Rheumatoid Arthritis," Rheumatology and Rehabilitation, vol. XVII, No. 3, pp. 155-163. 1978.

Scott et al., "McKeever Metallic Hemiarthroplasty of the Knee in Unicompartmental Degenerative Arthritis," The Journal of Bone and Joint Surgery, Feb. 1985, vol. 67-A, No. 2, pp. 203-207.

Wayne, "Use of the McIntosh Prosthesis in Surgical Reconstruction of the Knee," Abstracts of the 1971 Proceedings, Jun. 1972, No. 85, pp. 292-293.

Shin et al., "Posterior Lumbar Interbody Fusion via a Unilateral Approach," Yonsei Medical Journal, 2006, vol. 47, pp. 319-325.

Stauffer et al., "The MacIntosh Prosthesis, Prospective Clinical and Gait Evaluation," Arch Surg, Jun. 1975, vol. 110, pp. 717-720.

Steffen et al., "Effect of Implant Design and Endplate Preparation on the Compressive Strength of Interbody Fusion Constructs," Spine, 2000, vol. 25, No. 9, pp. 1077-1084.

Swanson et al., "Unicompartmental and Bicompartmental Arthroplasty of the Knee with a Finned Metal Tibial-Plateau Implant," The Journal of Bone and Joint Surgery, Oct. 1985, vol. 67-A, No. 8, pp. 1175-1182.

Synthes Spine, "510 (k) Summary—Revised Sep. 2007" 5 pages, Sep. 14, 2007West Chester, Pennsylvania.

Tan et al., Interbody Device Shape and Size are Important to Strengthen the Vertebra—Implant Interface, Spine 2005. vol. 30, No. 6, pp. 638-644.

Toth et al., "Polyehteretherketone as a biomaterial for spinal applications," Biomaterials, 2006, pp. 324-334.

Vadapalli et al., "Biomechanical Rationale for Using Polyetheretherketone (PEEK) Spacers for Lumbar Interbody Fusion—A Finite Element Study," Spine, 2006, vol. 31, No. 26, pp. E992-E998.

Vertebral Technologies, "InterFuse® Interbody Fusion System," 2009, pamphlet.

Wordsworth et al., "MacIntosh Arthroplasty for the rheumatoid knee: a 10-year follow up," Annals of the Rheumatic Diseases, 1985, pp. 738-741.

Zwillich, Artificial Spinal Disc Nears Approval. WebMD Medical News. Nov. 29, 2005. 4 pages. http://www.webmd.com/content/article/88/9801.htm.

Get ADR.com Top Surgeons—Latest Orthopedic Options, Nov. 29, 2005, 2 pages, http://www.getadr.com/link.htm.

(56) References Cited

OTHER PUBLICATIONS

Get ADR.com Top Surgeons—Latest Orthopedic Options, Nov. 29, 2005, 2 pages, http://www.getadr.com/maverick.htm.
Get ADR.com Top Surgeons—Latest Orthopedic Options (Artificial Disc Replacement), Nov. 29, 2005, 3 pages, http://www.getadr.com.
Get ADR.com Top Surgeons—Latest Orthopedic Options (Prestige Cervical ADR), Nov. 29, 2005, 3 pages, http://www.getadr.com/prestige.htm.
International Search Report and Written Opinion for Application Serial No. PCT/US2020/024290, dated Jun. 24, 2020, 8 pgs.

* cited by examiner

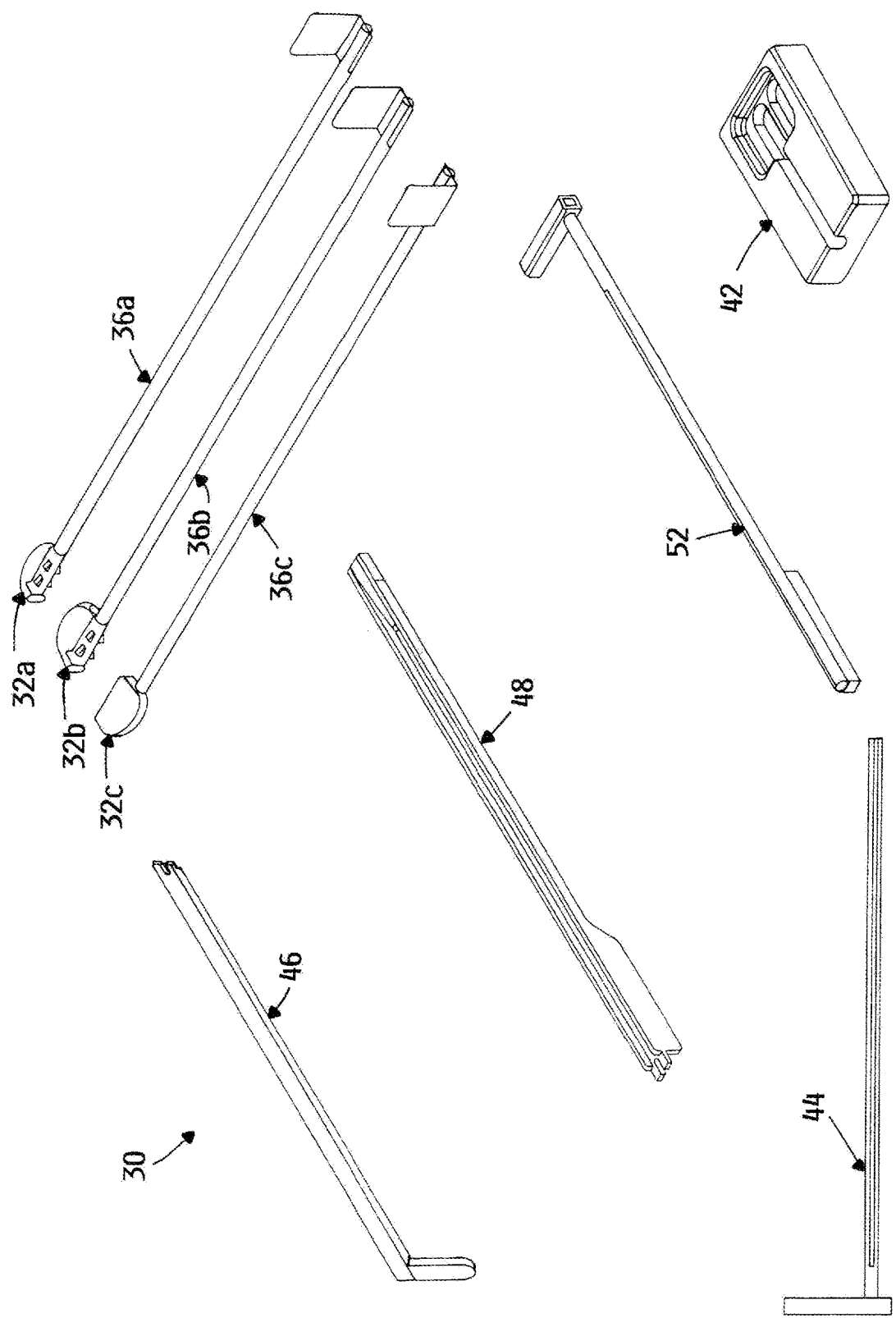

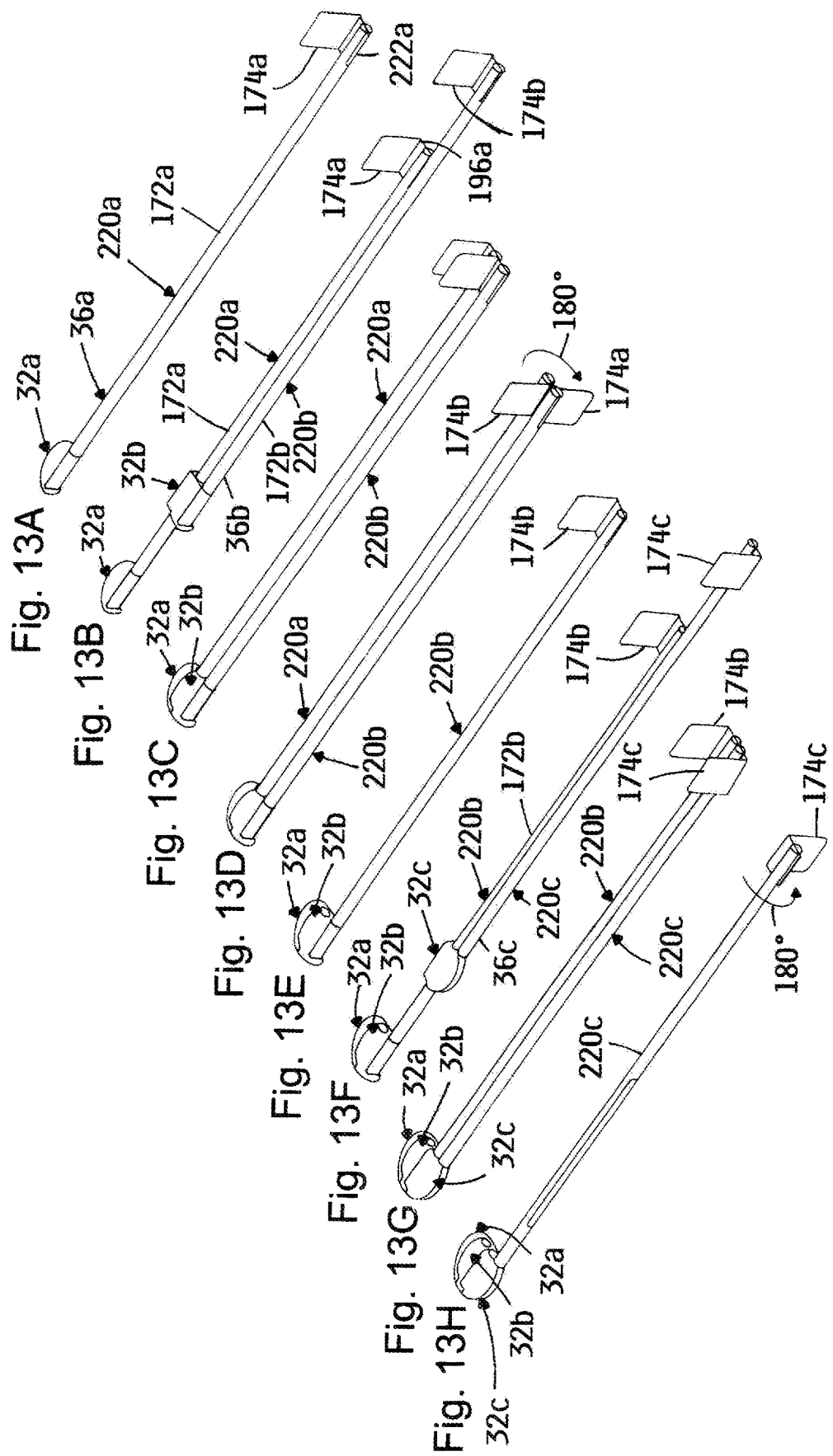

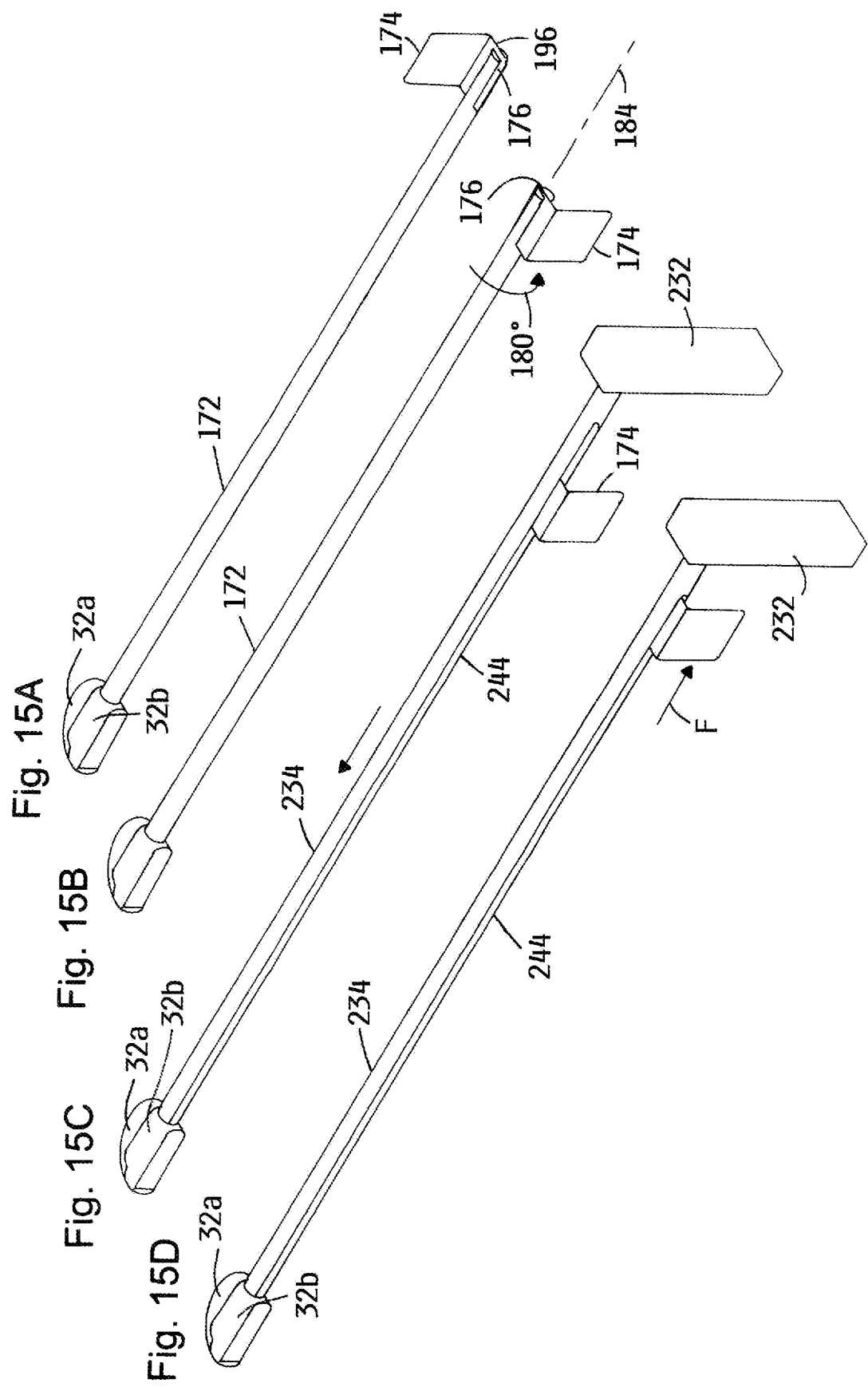

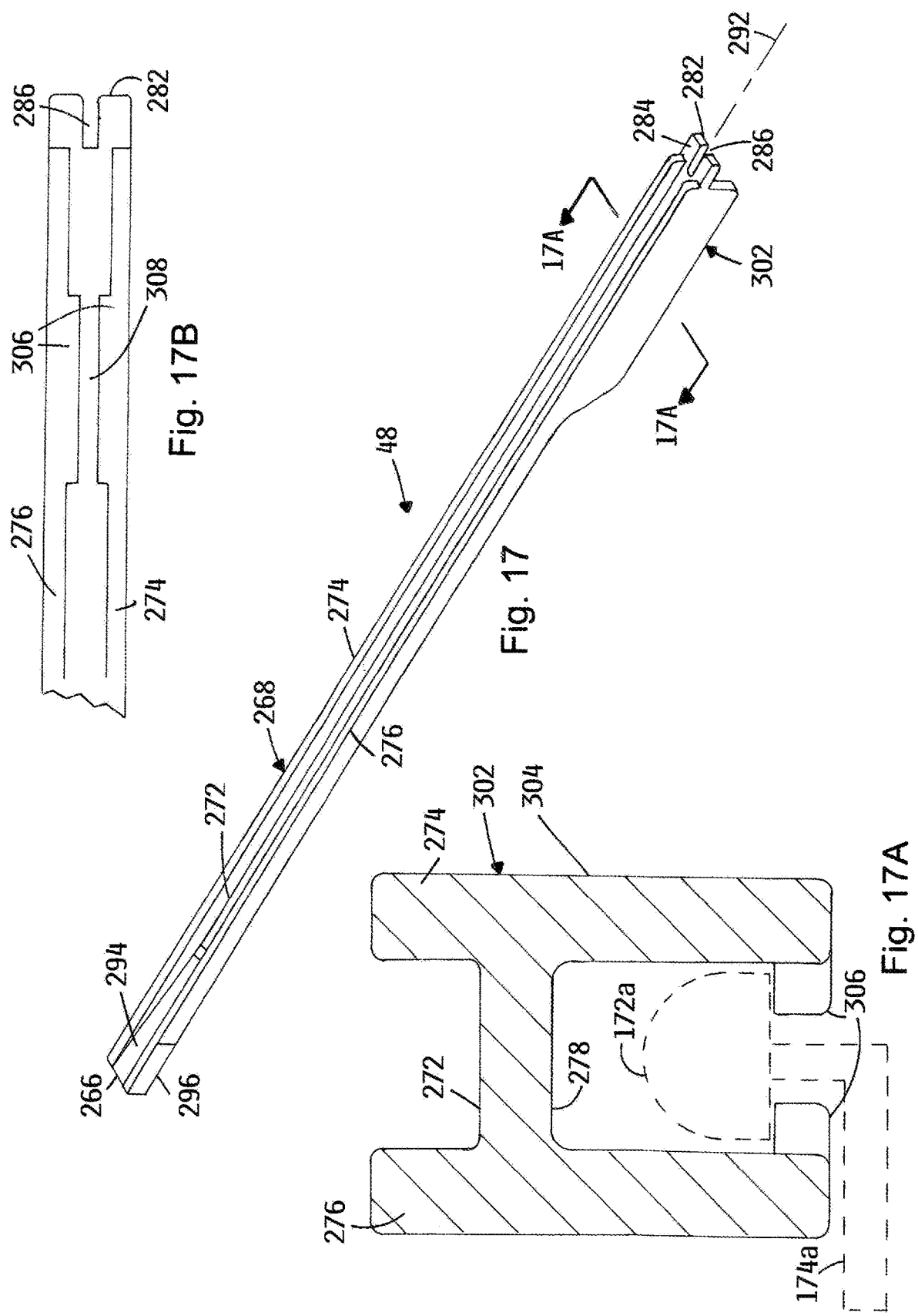

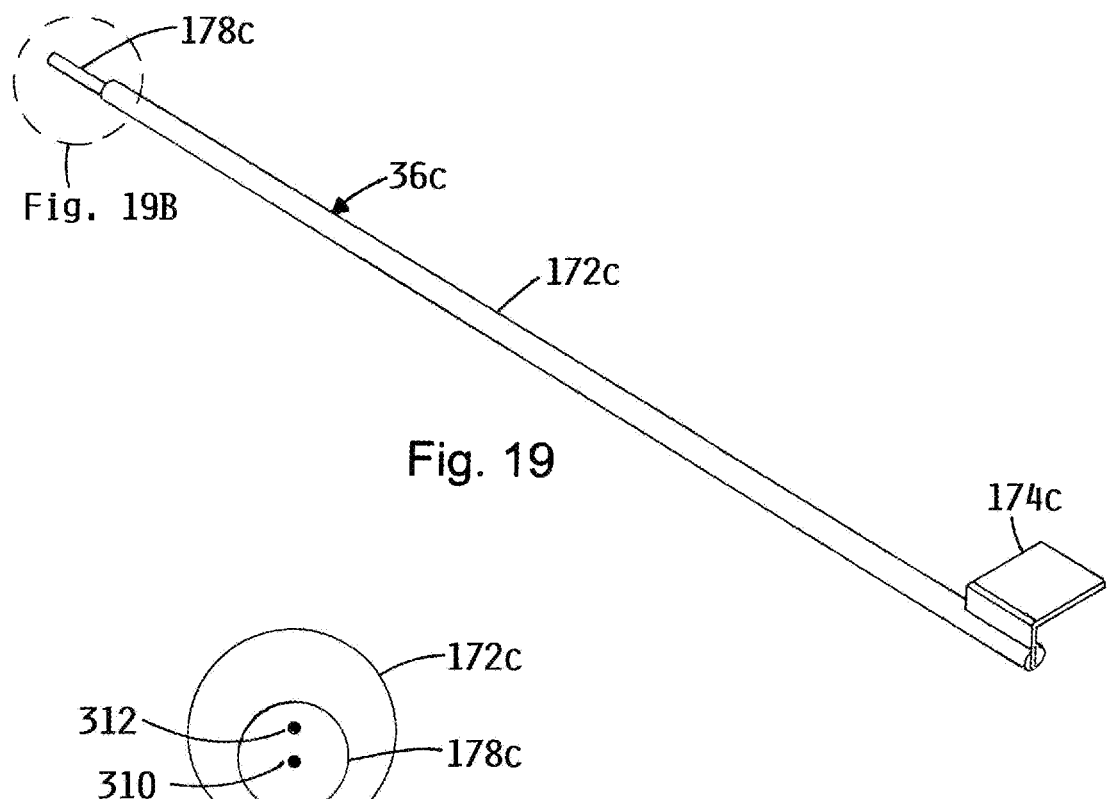
Fig. 19
Fig. 19A
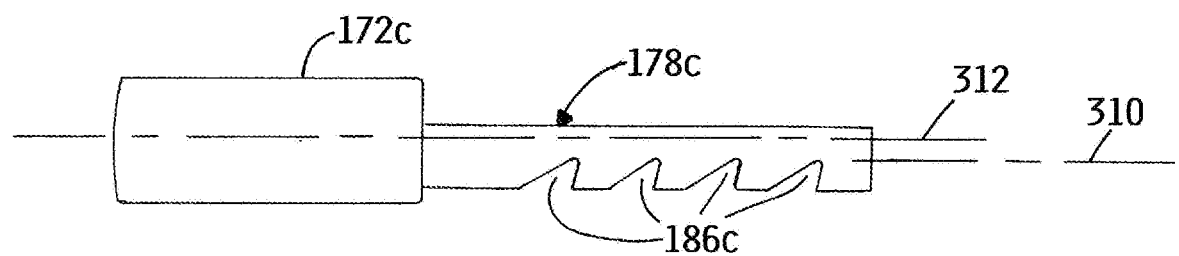
Fig. 19B

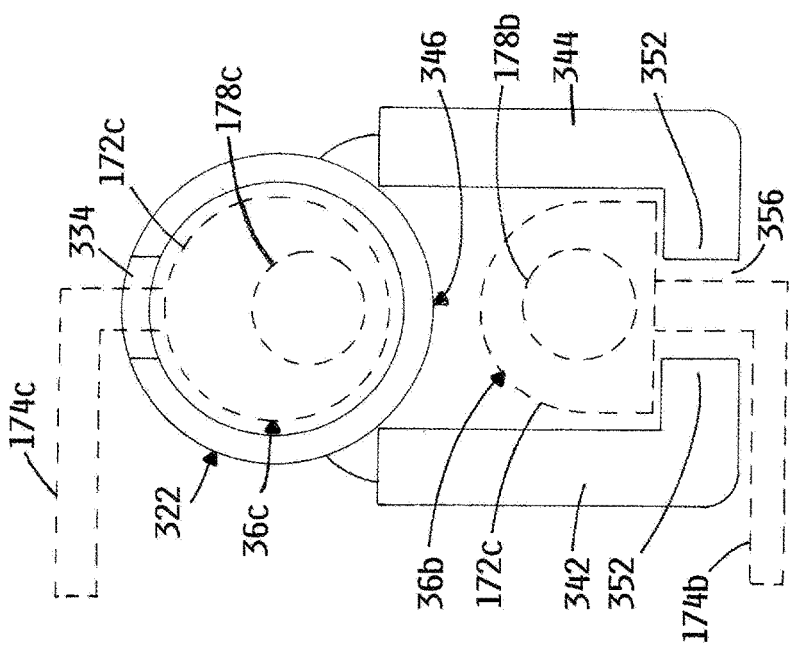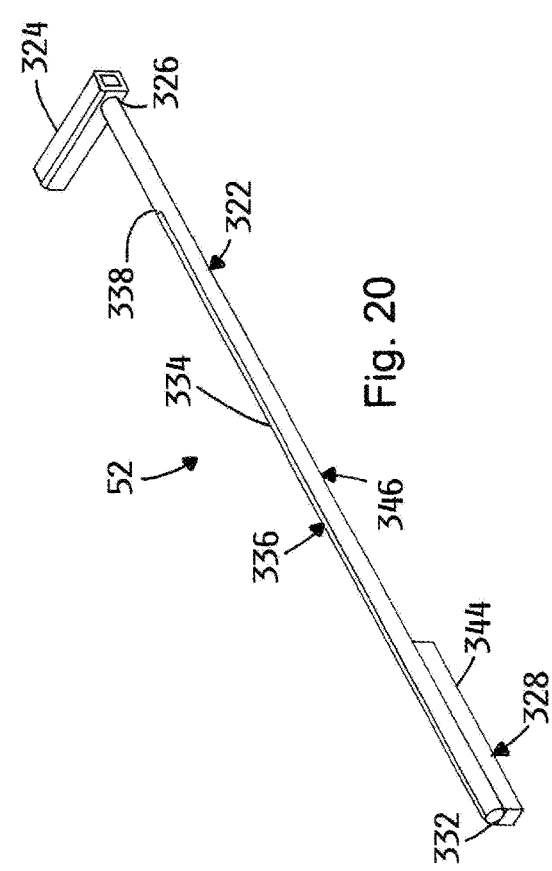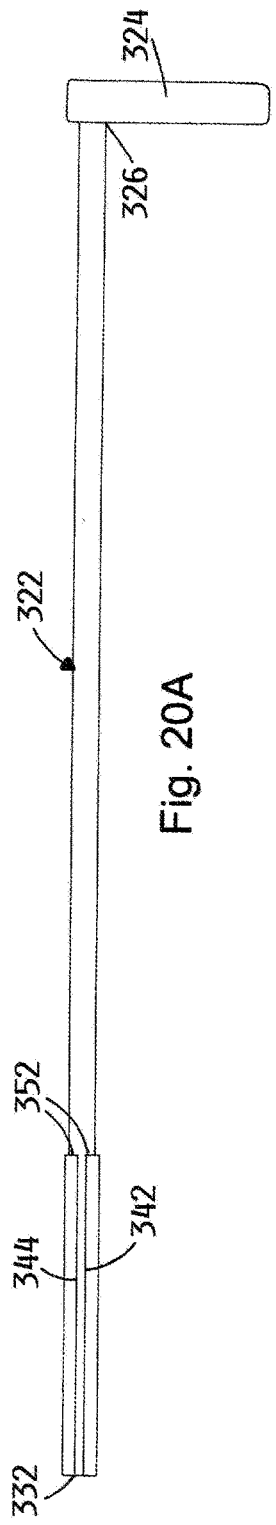

SURGICAL INSTRUMENT FOR IMPLANTING A SEMI-RIGID MEDICAL IMPLANT

REFERENCE TO RELATED APPLICATION

This application is a continuation-in-part of application Ser. No. 15/363,295, filed Nov. 29, 2016, which is a continuation of application Ser. No. 13/833,998, filed Mar. 15, 2013, which claims the benefit of U.S. Provisional Application No. 61/685,383, filed Mar. 16, 2012, the disclosure of which is incorporated herein in its entirety except for express definitions contained therein.

FIELD OF THE INVENTION

The invention relates generally to surgical instruments and methods of using such instruments. More particularly, the invention relates to a surgical instrument for implanting semi-ridged medical implants.

BACKGROUND OF THE INVENTION

Surgical instruments for accessing, handling and placing medical implants at various locations in a body are known, for example, from U.S. Pat. Nos. 7,549,995; 5,496,323; 8,080,004; 8,196,796; and 9,186,143 among others. Such instruments have proven particularly useful to surgeons when a medical implant needs to be placed in a hard to access location. For instance, in spinal fusion surgery where surgeons must navigate through complex anatomy such as internal organ and vasculature, in the instance of anterior lumbar fusion, or nerves, the spinal cord, and vasculature in the instance of posterior lumbar fusion, an appropriately sized, controllable, robust implant placement instrument is critical to the success of the surgery.

As minimally invasive surgical techniques have been developed, the surgical sub-specialties of orthopedics, spine, neurology, plastic and reconstructive, cardiovascular, and internal medicine, among others, have all benefited from the advancement of surgical instrumentation, including robotically assisted surgery, particularly when it is necessary to implant medical devices. Key to the utility of these instruments has been their ability to allow surgeons to successfully place a medical implant in body in a controlled manner.

Generally, the design of such instruments allows for a rigid connection of the implant and the insertion instrument. This construct aids in both the capture and remote transfer of directional energy from the surgeon to the implant as the implant is being placed. Typically, such surgical instruments have, at a minimum, means adapted to (1) orient an implant in relation to the surgical instrument function, typically attaching the implant at a distal end, and, (2) means that allow for the implant and surgical instrument to rigidly, but removeably, connect to one another. For instance, an instrument designed to connect to an implant may have a means that allows the instrument to engage with and rigidly secure the implant to the surgical instrument. See, for example, patents: U.S. Pat. Nos. 7,549,995; 6,830,574; and 6,746,454.

However, with advancements in material sciences, especially in the case of soft, durable, implantable compounds or substances, such as polymers, polyurethanes, polyimides, silicone resins, lignins, trimers, co-polymers, among others, various and metals new forms of implant designs have emerged that aim to treat previously un-treatable conditions or improve the function of currently known implant designs. Such improved implant designs may lack structural rigidity as a result of their material composition and may therefore be 'semi-rigid'.

A semi-rigid implant may be defined as an implant that lacks sufficient structural rigidity to withstand forces exerted upon it during surgical implantation without deforming, rotating, or otherwise deflecting from its intended implantation pathway. Such deformation, rotation, and deflection is not surgically optimal and may result in complications such as loss of the implant, breakage, tearing of soft tissues, pinching of veins, arteries, and nerves, and may result in device or surgical failures, especially in instances where one or more implant sub-assemblies are intended to connect to one another. This problem is exacerbated in the instances of robotic and navigation assisted surgery where precise and predictable implant control is critical to the placement of implants.

Implantable medical devices are well known and used by various surgical specialties to correct a variety of patient ailments. Across all implantable medical device types, surgeons are challenged with being as minimally disruptive to native anatomy and tissue as is practicable while still resolving their patient's problem.

For certain types of implantable medical devices, there exist limitations in form or function that necessitate the implantable medical device be of a size that is larger than ideal for minimally invasive surgical implantation. A strategy used to better align implantable medical device size and idealized invasiveness is to make the implantable medical device modular.

By making the implantable medical device modular, the implantable medical device may be implanted module by module through smaller incisions/pathways than would otherwise be possible. A modular implantable medical device is thus implanted and assembled at its final desired location within the body, but through a surgical access path(s) that minimizes undesired surgical trauma/native anatomy and tissue disruption.

Several modular implantable medical devices are known. One such device is disclosed in U.S. Pat. No. 7,392,089 showing an alignment and locking mechanism for an implantable medical device having an over-mold. U.S. Patent Publication No. 2008/0133017, U.S. Pat. Nos. 10,195, 048, and 9,510,953 discloses modular implantable medical devices for use in spinal surgery applications.

Another modular implantable medical device is disclosed in U.S. Pat. No. 7,097,663 and shows a modular ball and socket prosthesis with associated locking mechanism. In the above examples, the locking elements disclosed function through displacing, bending, or otherwise deforming material to facilitate locking. They also rely on material strength and/or material resistance to facilitate locking.

Implantable medical devices require tight tolerances and exacting specifications. These requirements are amplified for modular implantable medical devices. The implantable medical devices referenced in the above examples, while providing for module coupling and orienting, do so in a manner that invites problems such as unpredictable/difficult-to-control alignment, in-secure coupling/joining, and outright failure due to breakage. These short-comings are compounded in with semi-rigid modular implantable medical devices. Such problems are not desirable.

Accordingly, there is a need for an improved surgical handling instrument to facilitate the implantation of semi-rigid implants for advancement of patient benefit and medical implant innovation.

SUMMARY OF THE INVENTION

An embodiment of the invention is directed to a surgical instrument for implanting a semi-rigid medical implant. The surgical instrument includes a shaft, an accessory shaft, an actuation mechanism and an implant engagement mechanism. The shaft has a channel formed therein. The shaft has a proximal end and a distal end. The accessory shaft is slidably mounted in the channel. The accessory shaft has a proximal end and a distal end. The actuation mechanism is mounted to the shaft proximate the proximal end thereof. The actuation mechanism is capable of causing the accessory shaft to slide with respect to the shaft. The implant engagement mechanism is attached to the distal end of the accessory shaft. The implant engagement mechanism is capable of engaging a semi-rigid surgical implant.

Another embodiment of the invention is directed to a semi-rigid surgical implant that includes an implant body, a male engagement mechanism, a female engagement mechanism and a locking mechanism. The implant body has an opening formed therein. The implant body is fabricated from a semi-rigid material. The male engagement mechanism extends from an upper surface of the implant body. The female engagement mechanism is formed in a lower surface of the implant body. A shape of the male engagement body is complementary to the female engagement body. The locking mechanism is operably mounted to the implant body at least partially in the opening. The locking mechanism is deflectable from an undeflected configuration to a deflected configuration.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1 depicts various components of a disc nucleus replacement system in an embodiment of the invention.

FIGS. 13A through 13H depict the assembly of a modular nuclear disc prosthesis in an embodiment of the invention.

FIGS. 15A through 15D depict operation of the removal tool of FIG. 14 in an embodiment of the invention.

FIG. 17 is a perspective view of a B-segment stabilizer in an embodiment of the invention.

FIG. 17A is a sectional view of the B-segment stabilizer of FIG. 17 in an embodiment of the invention.

FIG. 17B is a partial plan view of the B-segment stabilizer of FIG. 17 in an embodiment of the invention.

FIG. 19 is a perspective view of a C-segment insertion tool in an embodiment of the invention.

FIG. 19A is an end view of the C-segment insertion tool in an embodiment of the invention.

FIG. 19B is a partial elevational view of the tip portion of the C-segment insertion tool of FIG. 19 in an embodiment of the invention.

FIG. 20 is a perspective view of a C-segment stabilizer C-segment insertion tool in an embodiment of the invention.

FIG. 20A is an elevational view of the C-segment stabilizer C-segment insertion tool of FIG. 20 in an embodiment of the invention.

FIG. 20b is an end view of the C-segment stabilizer C-segment insertion tool of FIG. 20 in an embodiment of the invention.

DETAILED DESCRIPTION OF THE INVENTION

Figure 2A:
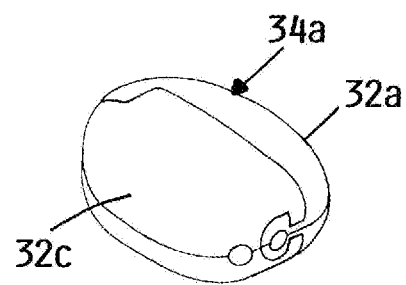
FIGS. 2A through 2D are perspective views of various modular disc nucleus prostheses embodiments of the invention.

Referring to FIG. 1, a disc nucleus replacement system 30 is depicted in an embodiment of the invention. The disc nucleus replacement system 30 includes modular segments 32a, 32b and 32c for assembly of modular disc nucleus prostheses 34a through 34d (FIG. 2) (hereinafter "the prosthesis" or "prostheses")", insertion tools 36a and 36c for installing the modular segments 32 of the prosthesis, and various tools to assist in the installation of the prosthesis, including a loading platform 42, a removal tool 44, an A-segment stabilizer 46, a B-segment stabilizer 48 and a C-segment stabilizer 52.

Throughout this disclosure, it is noted that certain components have numerical references consisting of a number followed by a letter suffix (e.g., modular segments 32a, 32b and 32c and insertion tools 36a and 36c above). Where this numbering convention is utilized, the number 10 refers to the item generically or collectively, and the letter to the item in particular. Following this convention, when the number is referred to alone, the reference is to the item generically or collectively (e.g., modular segment(s) 32 or insertion rod(s) 36).

Referring to FIGS. 2A through 2D (referred to collectively as FIG. 2) and FIGS. 3A through 3C (referred to collectively as FIG. 3), various prostheses and the modular segments from which they are constructed are depicted in embodiments of the invention. Each prosthesis 32a through 32d includes a plurality of modular segments 32 (i.e., at least two segments) interlocked with each other. Each modular segment 32 includes a superior side 62, an inferior side 64, a proximal end 66, and a distal end 68 opposite the proximal end 66.

The superior and inferior sides 62 and 64 of each modular segment 32 are disposed on opposing faces of a transverse plane 72a, 72b and 72c of the respective modular segment 32, the transverse planes 72a, 72b and 72c being orthogonal to a superior/inferior coordinate 74a, 74b and 74c of the respective modular segment 32a, 32b and 32c when in an implanted configuration.

Proximal/distal coordinates 76a, 76b and 76c are also defined as orthogonal to the superior inferior coordinates 74a, 74b and 74c and extending in a direction from the proximal ends 66 to the distal ends 68. Each of the plurality of modular segments 32 are adapted to interlock with an adjacent one of the plurality of modular segments in a side-by-side arrangement relative to the respective transverse planes 72 when in the implanted configuration.

The superior and inferior sides 62 and 64 are so named to correspond with their orientation along a respective superior/inferior coordinate 74 or superior/inferior direction when the prosthesis 34 is installed in an implanted configuration within the human body. In one embodiment, the modular segments 32 of the prosthesis 34 can be symmetric about the 11 transverse plane 72; that is, for this embodiment, the superior side 62 of each modular segment 32 is a mirror image of the inferior side 64 about the transverse plane 72, thus establishing the transverse plane 72 as a central transverse plane 78.

Figure 2B:
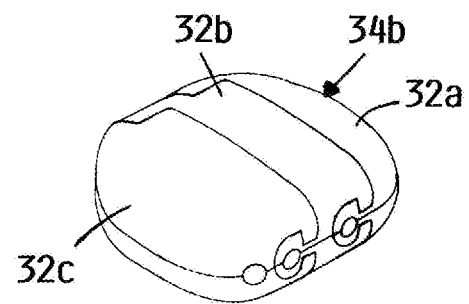
Figure 2C:
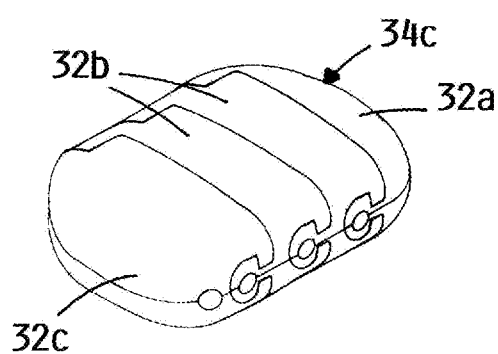
Figure 2D:
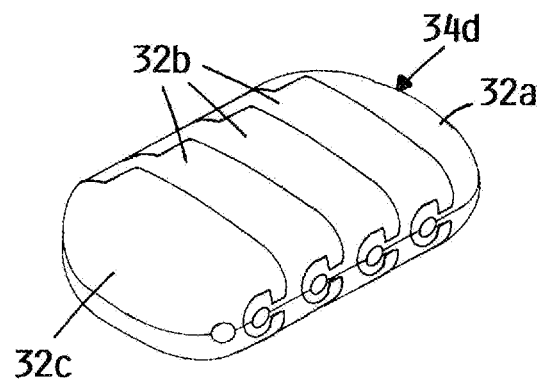
Figure 3C:
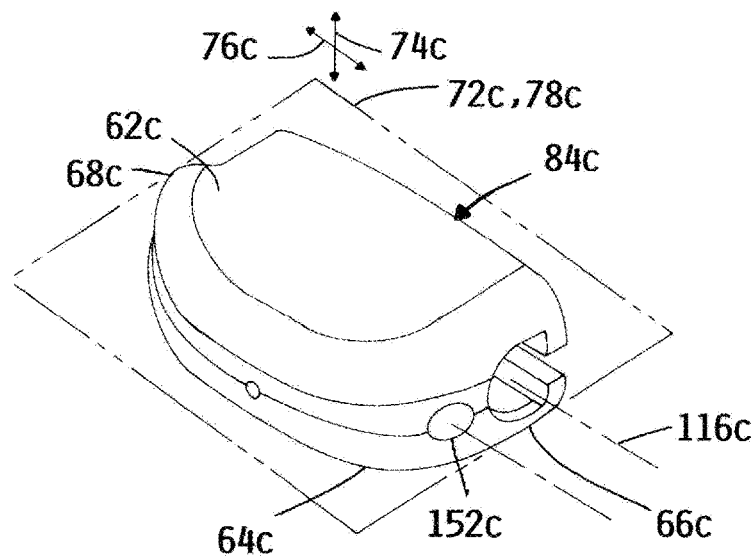
FIGS. 3A through 3C are perspective views of individual modular segments of the prostheses of FIGS. 2A through 2D in embodiments of the invention.
Figure 3B:
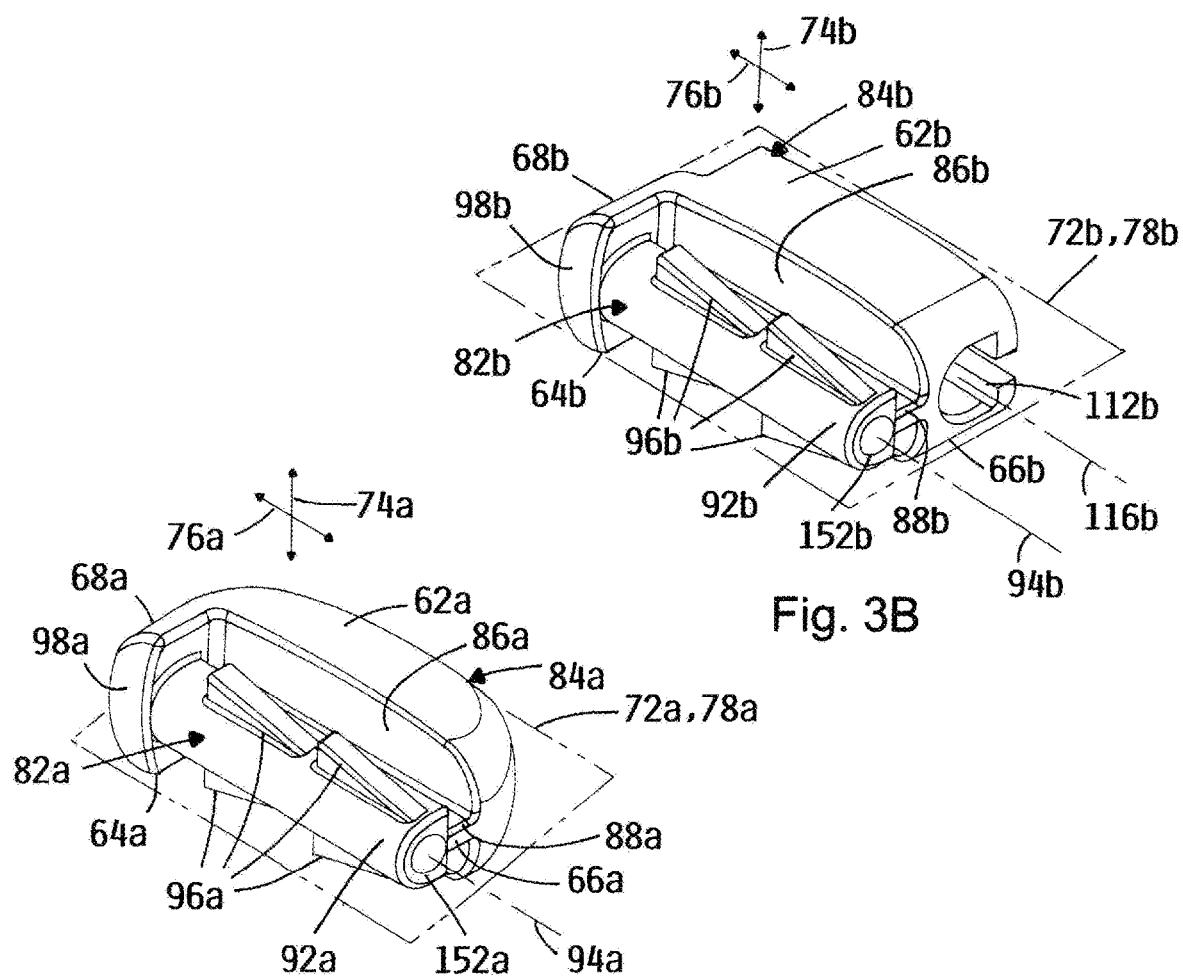
Figure 3A:
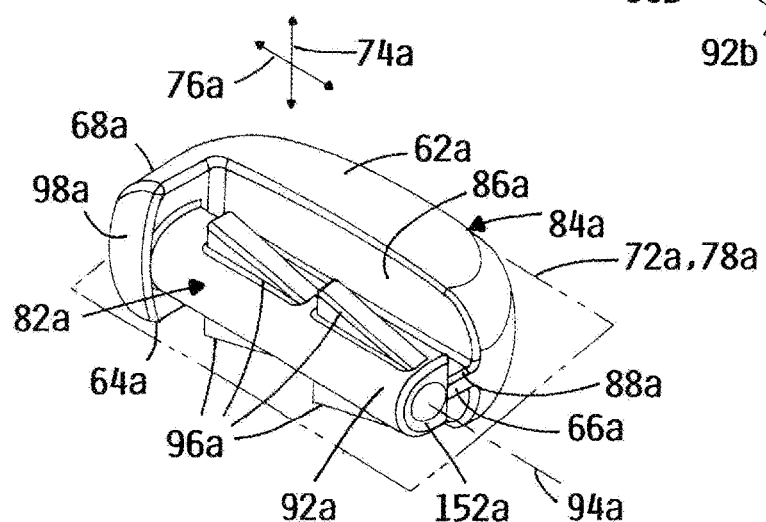

The prostheses depicted in FIG. 2 include up to three modular segment types, depicted in FIG. 3: the first end modular segment 32a, alternatively referred to herein as an "A" segment (FIG. 3A); the intermediate modular segment 32b, alternatively referred to herein as a "B" segment (FIG. 3B); and the opposing end modular segment 32c, alternatively referred to herein as a "C" segment (FIG. 3C). In various embodiments of the invention, prostheses 34 can include one or more B-segments 32b, or can have no B-segments 32b (i.e., the A-segment 32a is coupled directly to the C-segment 32c, as depicted in FIG. 2A). While the length, width and thickness dimensions of individual B-segments 32b can vary, the general characteristics are the same, as described below. In some embodiments employing multiple B-segments 32b, the B-segments 32b are identical.

Referring to FIG. 4 and again to FIG. 3A, the first end modular segment 32a (A-segment) is depicted in an embodiment of the invention. The first end modular segment 32a includes a body portion 84a and a rail portion 82a, the rail portion 82a extending from a flanking face 86a of the body portion 84a. In one embodiment, the rail portion 82a includes a web 88a and a rail head 92a, the flanking face 86a and the rail head 92a being separated by the web 88a. The rail head 92a can define a rail axis 94a that passes through the proximal and distal ends 66a and 68a of the modular segment 32a.

Figure 4:
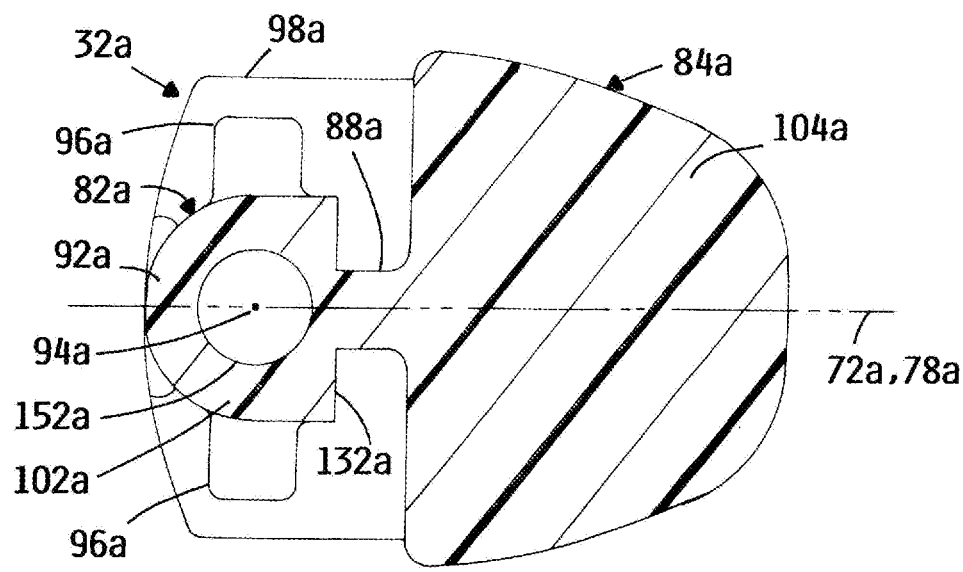
FIG. 4 is a sectional view of a first end modular segment ("A-segment") in an embodiment of the invention.

The rail portion 82a can also include a plurality of diametrically opposed barb portions 96a that extend radially outward relative to the rail axis 94a and parallel to the superior/inferior coordinate 74a of the first end modular segment 32a. In one embodiment, 12 the first end modular segment 32a includes a stop portion 98a located at the distal end 68a. Cross-sections 102a and 104a of the rail portion 82a and the body portion 84a, respectively, of the first end modular segment 32a are depicted at FIG. 4, the cross-sections 102a, 104a being normal to the rail axis 94a.

Herein, the rail portion 82a, rail axis 94a, rail portion cross-section 102a, body portion 82a and body portion cross-section 104a of the first end modular segment 32a are alternatively referred to as the first end rail portion 82a, first end rail axis 94a, first end rail cross-section 102a, first end body portion 82a, and first end body portion cross-section 104a, respectively, to clarify association with the first end modular segment 32a.

Referring to FIGS. 5 and 6 and again to FIG. 3B, the intermediate modular segment 32b (B-segment) is depicted in an embodiment of the invention. The intermediate modular segment 32b includes a body portion 82b and a rail portion 82b, the rail portion 82b extending from a flanking face 86b of the body portion 82b. In one embodiment, the rail portion 82b includes a web 88b and a rail head 92b, the flanking face 86b and the rail head 92b being separated by the web 88b. The rail head 92b can define a rail axis 94b that passes through the proximal and distal ends 66b and 68b of the modular segment 32b.

Figure 5:
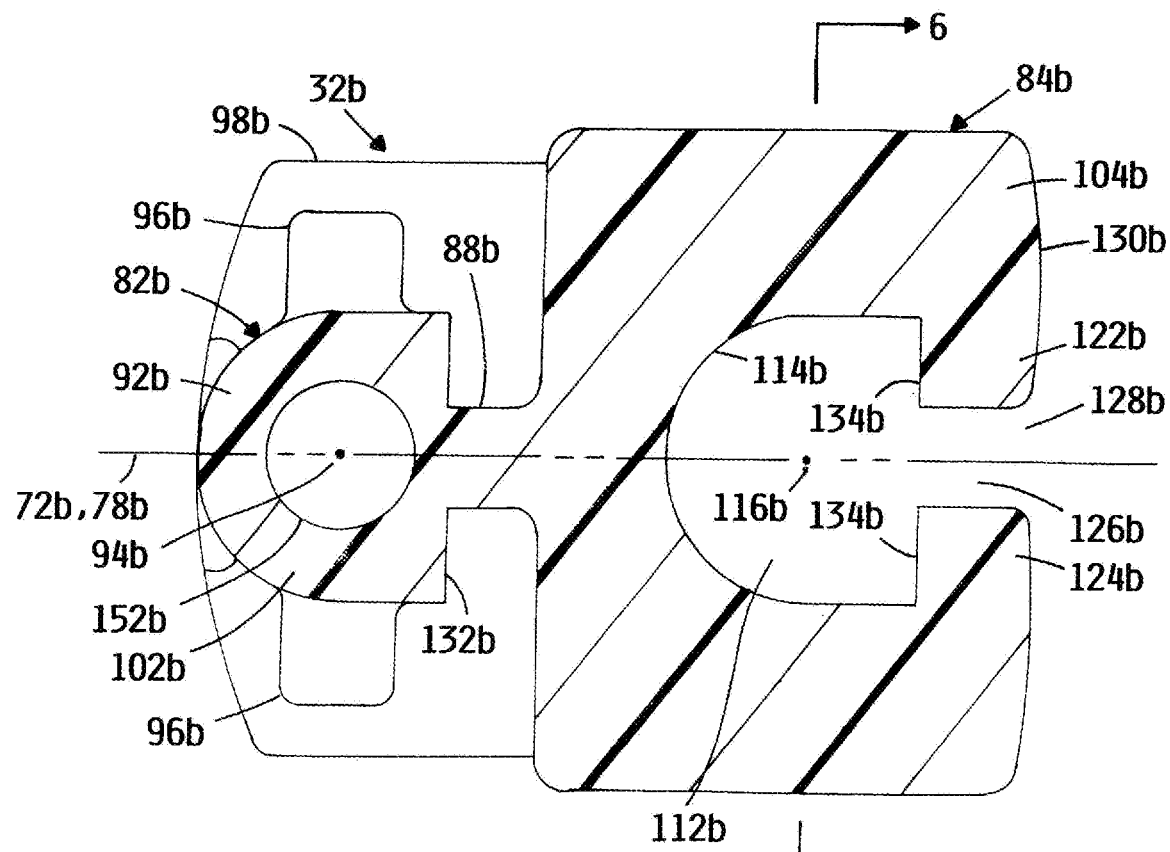
FIG. 5 is a sectional view of an intermediate modular segment ("B-segment") in an embodiment of the invention.

The rail portion 82b can also include a plurality of diametrically opposed barb portions 96b that extend radially outward relative to the rail axis 94b and parallel to the superior/inferior coordinate 74b of the intermediate modular segment 32b. In one embodiment, the intermediate modular segment 32b includes a stop portion 98b located at its distal end. Cross-sections 102b and 104b of the rail portion 82b and the body portion 84b, respectively, of the intermediate modular segment 32b are depicted at FIG. 5, the cross-sections 102b, 104b being normal to the rail axis 94b.

Figure 6:
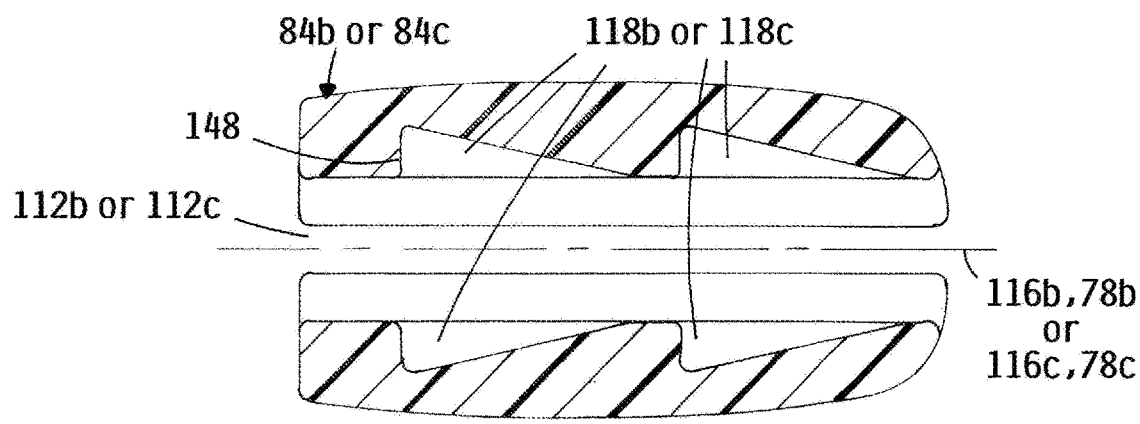
FIG. 6 is a sectional view of an elongate slot portion of the modular segments of FIGS. 4 and 5 in an embodiment of the invention.

The body portion 84b of the intermediate modular segment 32b defines an elongate slot 112b that passes through the body portion 84b and includes an interior surface 114b. The elongate slot 112b further defines a slot axis 116b that is substantially parallel to the intermediate rail axis 94b of the intermediate modular segment 32b. In one embodiment, the rail axis 94b and the slot axis 116b lie on the transverse plane 72b of the intermediate modular segment 32b. In the depicted embodiment, the transverse plane 72b corresponds to the central transverse plane 78b. The body portion 84b can also include a plurality of recesses 118b that extend parallel to the superior/inferior coordinate 74b in both the superior and inferior directions relative to the slot axis 116b (FIG. 6).

Herein, the rail portion 82b, rail axis 94b, rail portion cross-section 102b, body portion 84b, elongate slot 112b, slot axis 116b and body portion cross-section 104b of the intermediate modular segment 32b are alternatively referred to as the intermediate rail portion 82b, intermediate rail axis 94b, intermediate rail portion cross-section 102b, intermediate body portion 84b, intermediate elongate slot 112b, intermediate slot axis 116b and intermediate body portion cross-section 104b, to clarify association with the intermediate modular segment 32b.

The intermediate body portion 84b can also be characterized as having a superior lip portion 122b and an inferior lip portion 124b, each being named for their location along the superior/inferior coordinate 74b relative to the transverse plane 72b. The lip portions 122b, 124b are adjacent to and partially define the intermediate elongate slot 112b, and protrude toward each other.

A gap 126b is defined between the superior lip portion 122b and the inferior lip portion 124b, defining an open side 128b of the elongate slot 112b. In the depicted embodiment, each lip portion 122b, 124b protrudes toward the central transverse plane 78b. The lip portions 122b 14 and 124b can also define an opposing flanking face 130b that faces in a direction opposite the flanking face 86b of the intermediate body portion 84b.

Figure 7:
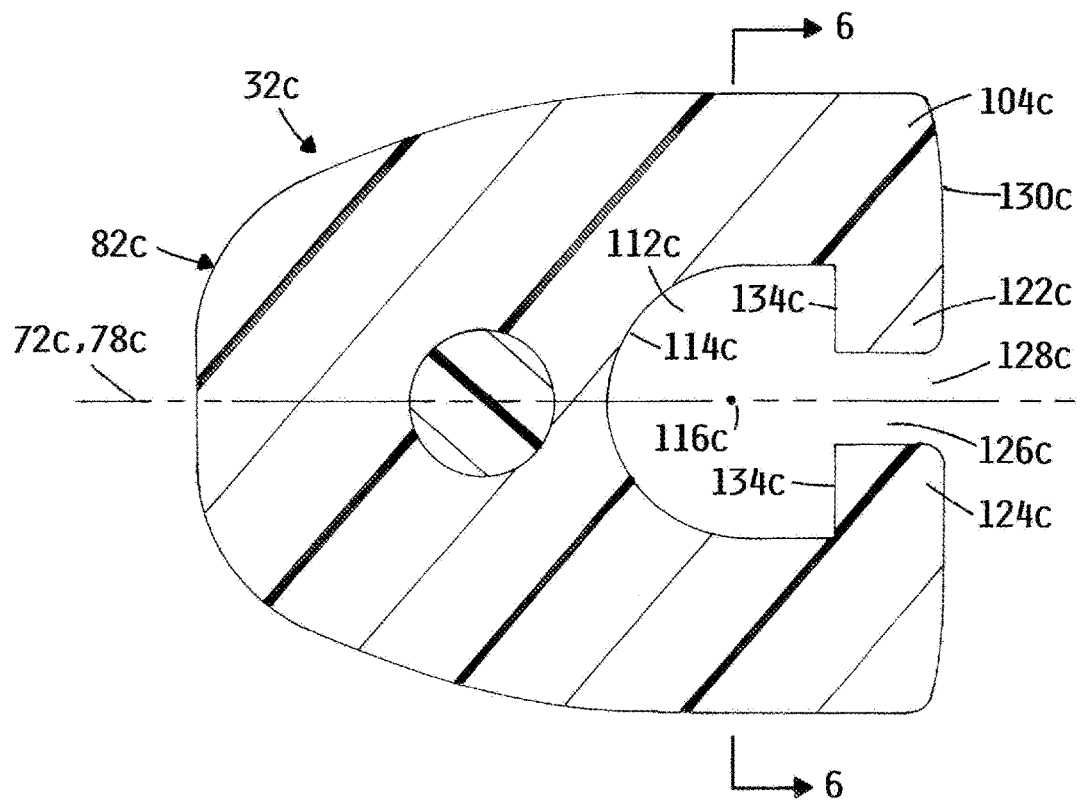
FIG. 7 is a sectional view of an opposing end modular segment ("C-segment") in an embodiment of the invention.

Referring to FIG. 7 and again to FIG. 6, the opposing end modular segment 32c (C-segment) is depicted in an embodiment of the invention. (It is noted that the cross-section depicted in FIG. 6 applies to both FIGS. 5 and 7). The opposing end modular segment 32c includes a body portion 84c that defines an elongate slot 112c, the elongate slot 112c further defining a slot axis 116c that lies on the transverse plane 72c. The elongate slot 112c includes an interior surface 114c and passes through the body portion 84c of the opposing end modular segment 32c. The body portion 84c includes a body portion cross-section 104c that is normal to the slot axis 116c.

The body portion 84c of the opposing end modular segment 32c can also include a superior lip portion 122c and an inferior lip portion 124c having the same characteristics as the superior and inferior lip portions 122b and 124b of the intermediate modular segment 32b. The body portion 84c of the opposing end modular segment 32c can further define a plurality of recesses 118c that are recessed from the interior surface 114c of the elongate slot 112c of the body portion 84c. The recesses 118c can extend radially outward relative to the slot axis 116c and are parallel to the superior/inferior coordinate 74c of the opposing end modular segment 32c.

Herein, the body portion 84c, elongate slot 112c, slot axis 116c and body portion cross-section 104c of the opposing end modular segment 32c are alternatively referred to as the opposing end body portion 84c, opposing end elongate slot 112c, opposing end slot axis 116c and opposing end body portion cross-section 104c, to clarify association with the opposing end modular segment 32c.

The rail heads 92 can each include faces 132 that are substantially planar and substantially parallel to the respective superior/inferior coordinate 74, the faces 132 thereby being at a right angle relative to the respective web portion 88. The body portion 84 of the adjacent, mating modular segment 32, being complementary to the rail portion 82, can include the superior and inferior lip portions 122 and 124 that also include interior faces 134 that are substantially planar and substantially parallel to the superior/inferior coordinate 74 (e.g., FIGS. 5 and 7).

Figure 8:
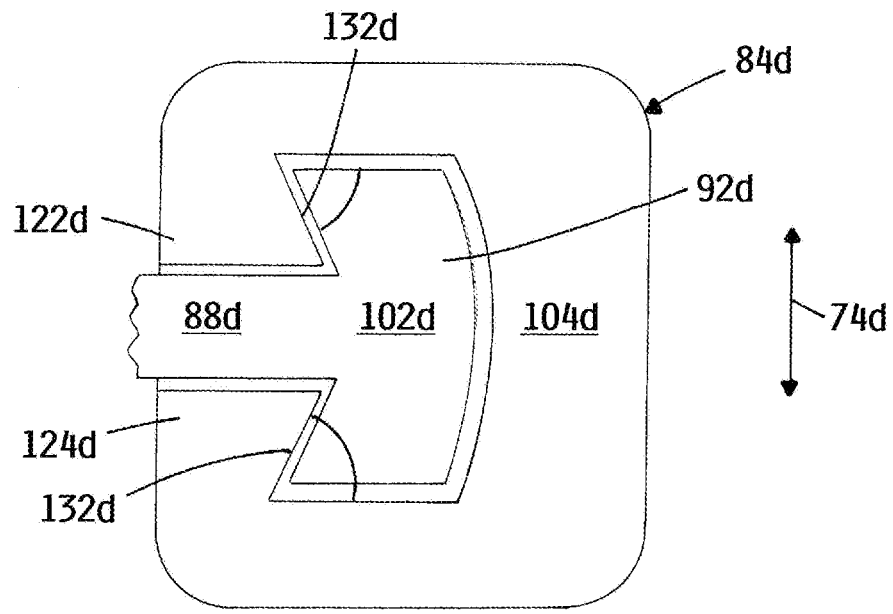
FIG. 8 is a partial sectional view of an alternative rail portion and body portion configuration in an embodiment of the invention.

Referring to FIG. 8, an alternative rail cross-section 102d and mating body portion cross section 104d is presented in an embodiment of the invention. For these embodiments, lip portions 122d, 124d also include faces 132d that are each substantially planar, but each being oblique relative to the superior/inferior coordinate 74d so as to define a "dovetail" profile. That is, the planar faces 132d of the rail head 92d that are adjacent the web 88d for the rail portion 82d intersect web 88d at an acute angle θ. The body portion 84d of the adjacent, mating segment, being complementary, also defines an acute angle θ relative the web portion 88d.

Functionally, the right angle or acute angle configurations between the faces 132 and the web portion 88 enhance the mechanical coupling between adjacent segments in a direction that is normal to both the superior/inferior coordinate 74 and rail axis 94. These configurations rely primarily on compressive contact between the engaged segments and less on friction between the segments, thereby providing for a positive mechanical coupling therebetween.

The enhanced coupling is particularly advantageous when the segments comprise a soft or compliant material having a relatively low hardness. A non-limiting example of a soft or compliant material is a polymer such a biocompatible polyurethane. A non-limiting example of a hardness of a soft or compliant material is a material with a durometer hardness ranging from about Shore 18 A to about Shore 55D. A further and non-limiting example of a soft or compliant material is a material with a compressive modulus between about 2 and about 100 MPa. In a preferred embodiment, the compressive modulus is between about 6 and about 20 MPa.

The cross-sections 102 and 104 of the various rail portions 82 and the various body portions 84 can be configured to be complementary to itself and the other modular segments 32. That is, the various rail portion cross-sections 102 can be shaped and dimensioned to mate with the various body portion cross-sections 104. Likewise, the various recesses 118 can be positioned and dimensioned to accept (i.e., to be complementary with) the barb portions 96 on the various rail portions 82 of the modular segments 32.

In this way, a given A-segment 32a can be coupled to either a given B-segment 32b or a given C-segment 32c, a given C-segment 32c can be coupled with either a given A-segment 32a or a given B-segment 32b, and a given B-segment 32b can be coupled with another B-segment 32b. The modularity of the system enables the construction of a variety of prosthesis sizes by interlocking the various segments together in a side-by-side manner, the A, B and C-segments 32a, 32b and 32c constituting the building blocks of the modular system.

Figure 18A:
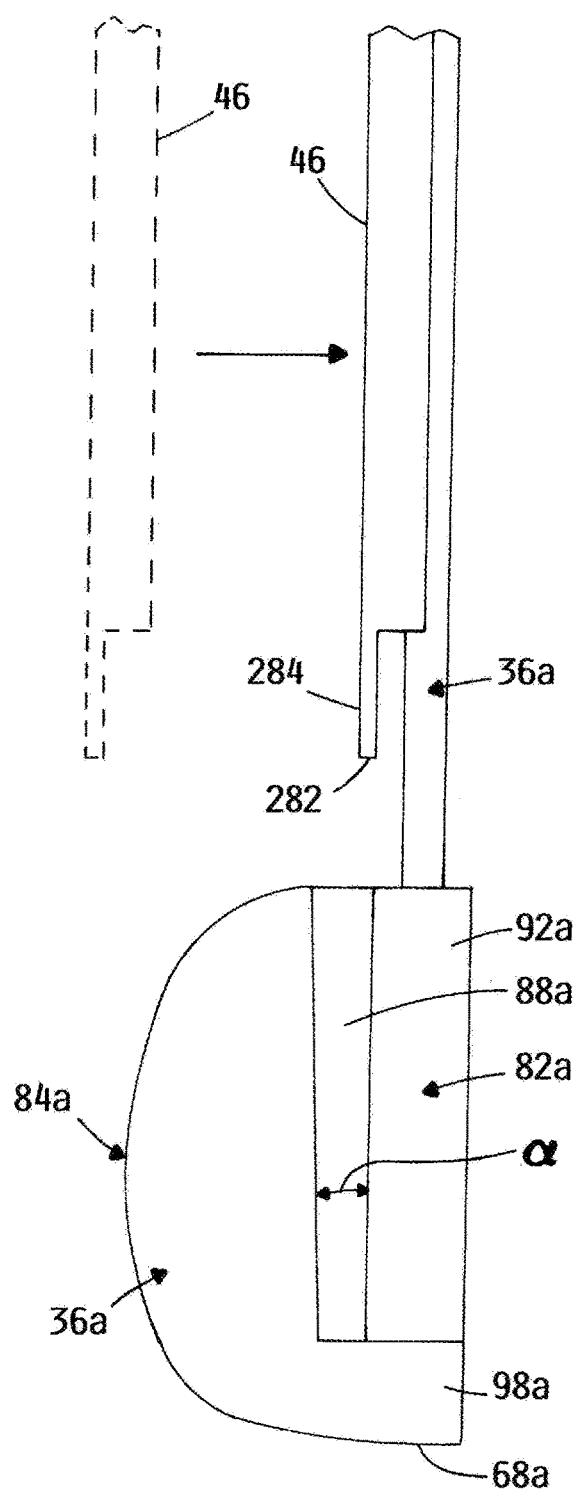
FIGS. 18A and 18B are plan views depicting the coupling of the A-segment stabilizer to an A-segment/insertion tool assembly in an embodiment of the invention.

In certain embodiments, the flanking faces 86 of the various segments are oblique relative to the rail axes 94 (i.e., are not parallel to the rail axes 94). Instead, the flanking faces 86 slope slightly towards the rail axes 94 at an angle from the proximal end 66 to the distal end 68, as best seen in FIG. 18A. That is, the flanking faces 86 are spaced further from the rail axes 94 at the proximal ends 66 than at the distal ends 68. Thus, for embodiments that include this aspect, the rail axis 94 of a given modular segment 32 will intersect plane of the respective flanking face 86 at a point distal to the modular segment 32.

To accommodate the oblique flanking face configuration, the lip portions 122, 124 of the modular segments 32b and 32c can be of varying thickness from the proximal end 66 to the distal end 68 of the respective body portion 84b, 84c. While the interior face 134 of a given lip portion 122, 124 is parallel to the respective slot axis 116, the thickness of the lip portions 122, 124 (i.e., the dimension normal to the slot axis 116) can decrease from the proximal end 66 to the distal end 68, so that the lip portions 122, 124 themselves form a complementary oblique interface with the oblique flanking face 86 of the adjacent modular segment 32a or 32b.

Figure 9:
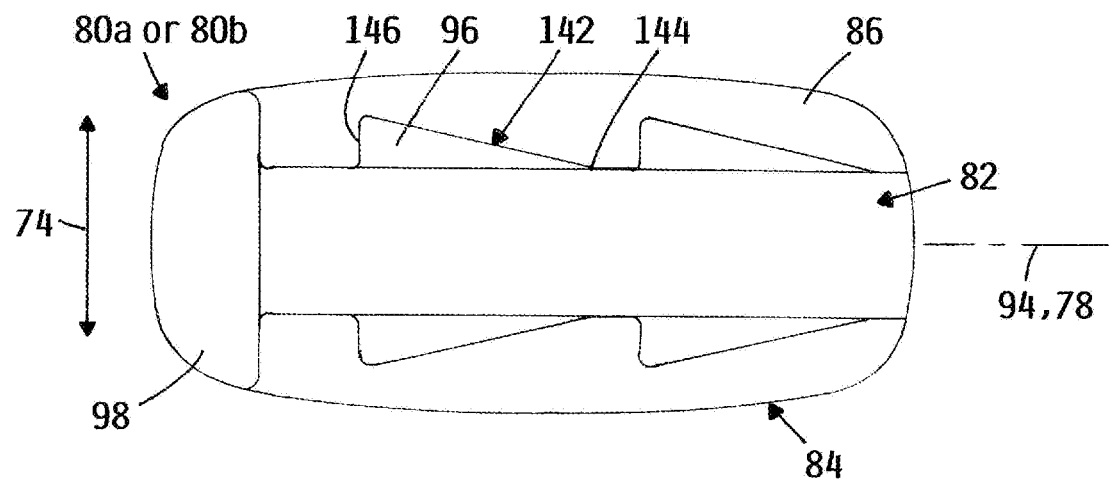
FIG. 9 is a side view of an A-segment or a B-segment in an embodiment of the invention.

Referring to FIG. 9, a side view of a modular segment 32a or 32b is presented in an embodiment of the invention. The barb portions 96 can each define an inclined profile 142. The inclined profile 142 intersects an outer surface of the rail portion 82 at an intersection point 144 on the proximal end of the barb portion 96. From the intersection point 144, the dimension of the barb portion increases toward a distal end 146 of the barb portion 96.

In the depicted embodiments, the distal ends 146 of the barb portions 96 are parallel to the superior/inferior coordinate 74 of the respective modular segment 32. Thus, in this embodiment, the barb portions 96 each define a right-triangular profile in a plane that is parallel to both the superior/inferior coordinate 74 and the rail axis 94 of a given segment 32a, 32b.

In one embodiment, the corresponding recesses 118 of the body portion 84 of the adjacent modular segment 32b or 32c can define a similar, triangular shape that is complementary to the triangular shape of the barb portion 96 (FIG. 6). In other embodiments the recesses 118 can be, for example, rectangular, so long as a distal boundary 148 of the recesses 118 are complementary to the distal ends 146 of the barb portions 96.

For assembly of the implant of, for example, FIG. 2b, the B-segment 32b is positioned proximal to the proximal end of the A-segment 32a, so that the slot axis 116b of the body portion 84b of the B-segment 32b is substantially concentric with the rail axis 94a of the rail portion 82a of the A-segment 32a. The body portion 84b of the B-segment 32b is then slid over the rail portion 82a of the A-segment 32a in the distal direction along the rail axis 94a until the barb portions 96a of the rail portion 82a are captured within the recesses 118b of the body portion 84b of the B-segment 32b. The distal end 68b of the body portion 84b of the B-segment 32b can be substantially registered against the stop portion 98a of the A-segment 32a when the barb portions 96a of the A-segment 32a are secured within the recesses 118b of the B-segment 32b.

As the body portion 84b of the B-segment 32b is slid over the rail portion 82a of the A-segment 32a, the interior surface 114b of the elongate slot 112b of the B-segment 32b rides over the protruding barb portions 96a of the A-segment 32a. This interaction causes the barb portions 96a of the A-segment 32a to be compressed and the wall of the body portion of the B-segment 32b to deflect upwards. However, once the barb portions 96a are registered within the respective recess 118b, there is essentially no deformation of the components.

After the B-segment 32b is secured to the A-segment 32a, the C-segment 32c is positioned proximal to the proximal end of the B-segment 32b, so that the slot axis 116c of the body portion of the C-segment 32c is substantially concentric with the rail axis 94b of the B-segment 32b. The body portion 82c of the C-segment 32c is then slid over the rail portion 82b of the B-segment 32b in the distal direction along the rail axis 94b until the barb portions 96b of the rail portion 82b are captured within the recesses 118c of the body portion 84c of the C-segment 32c. The distal end 68c of the body portion 84c of the C-segment 32c can be substantially registered against the stop portion 98b of the B-segment 32b when the barb portions 96b of the B-segment 32b are secured within the recesses 118b of the C-segment 32c.

For a 2-segment implant (FIG. 2A), the C-segment 32c is interlocked directly to the A-segment 32b in similar fashion. Likewise, for an implant having four or more segments, additional intermediate B-segments are interlocked in similar fashion. As a non-limiting example, embodiments can have as many as 8 modular segments (one A-segment 32a, one C-segment 32c, and six B-segments 32b).

Functionally, the various structural aspects of the rail and slot portions 82, 112 of the modular segments 32 prevent relative motion between the modular segments 32 in all directions, even where a relatively soft or compliant material is utilized for the modular segments 32. The engagement of a given rail portion 82 with an adjacent body portion 84 prevents relative motion between the engaged segments along the superior/inferior coordinates 74.

Engagement between the barb portions 96 and stop portions 98 of a given modular segment 32, when engaged with an adjacent segment 32, prevent relative motion between the engaged segments 32 along the proximal/distal coordinates 76. Both the lip portions 122 and 124 and the barb portions 96 provide shear resistance to movement parallel to the transverse plane 72. The superior and inferior lip portions 122 and 124 of a given modular segment 32, along with the barb portions 96 of an adjacent, engaged modular segment 32, prevent separation of the modular segments 32.

The inclined profile 142 of the barb portions 96 enable the body portion 84 of an adjacent segment 32 to be more easily slid over the barb portions 96 as the adjacent segment 32 is moved in the distal direction relative to the given segment 32. However, once the barb portions 96 are registered within their corresponding recesses 118, the distal ends 146 of the barb portions 96 interact with the distal boundaries 148 of the recesses 118 to prevent the adjacent segment from moving along the proximal/distal coordinate 76.

For embodiments utilizing oblique flanking faces 86, there is little or no sliding interference between the flanking faces 86 and the superior and inferior lip portions 122 and 124 of adjacent segments until the adjacent segments are at or near the implanted position. This helps limit the frictional load during assembly.

Figure 10:
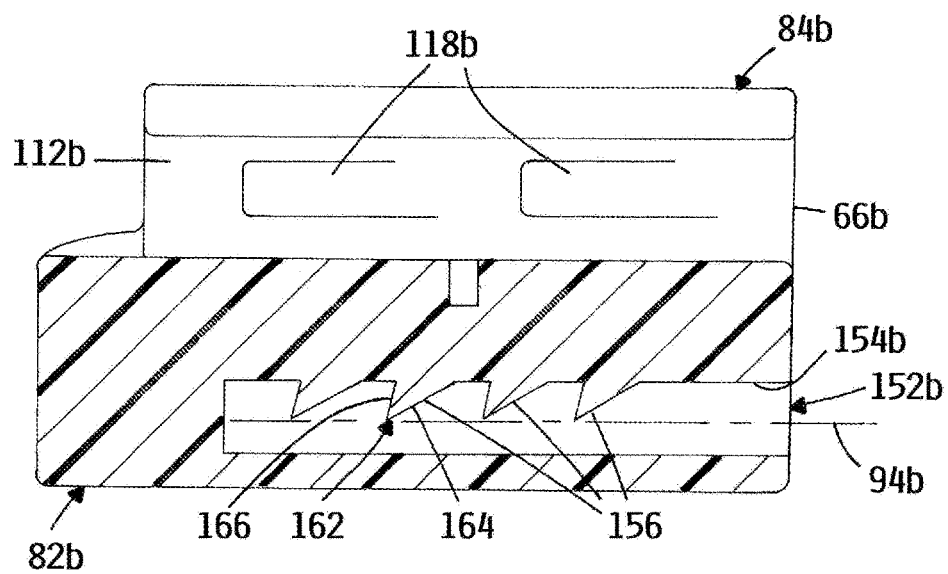
FIG. 10 is a sectional view of a B-segment at the transverse plane in an embodiment of the invention.

Referring to FIG. 10, a cross-section of a B-segment 32b that cuts through the transverse plane 72b is presented depicting a mounting port 152b in an embodiment of the invention. The modular segments 32 can each include such a mounting port 152 for mounting the respective modular segment 32 to an insertion tool. While the discussion below is directed to the mounting port 152b, the general aspects apply to all mounting ports 152.

In one embodiment, the mounting port 152b defines a substantially cylindrical cavity 154b that is concentric about the rail axis 94b of the modular segment 32b and is accessible from the proximal end 66b of the modular segment 32b. The mounting port 152b can further include internal detents 156 that extend from one side of an internal wall 158b of the mounting port 152b. In one embodiment, the detents 156 can each define a triangular or right triangular profile 162, wherein a proximal face 164 of each detent 156 is inclined relative to the rail axis 94b and a distal face 166 of the detent 156 is orthogonal to or only slightly acute relative to the rail axis 94b.

Figure 11:
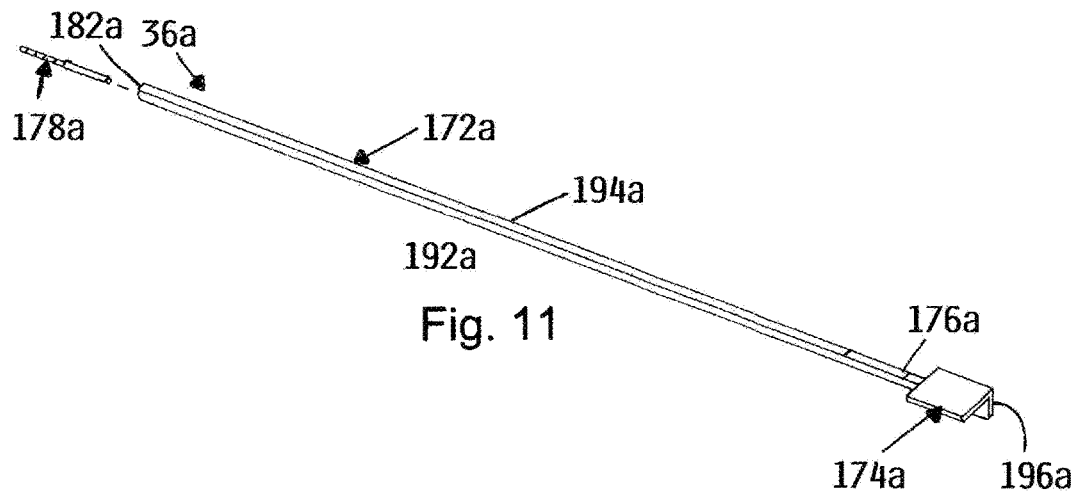
FIG. 11 is an exploded view of an A/B insertion tool in an embodiment of the invention.
Figure 11A:
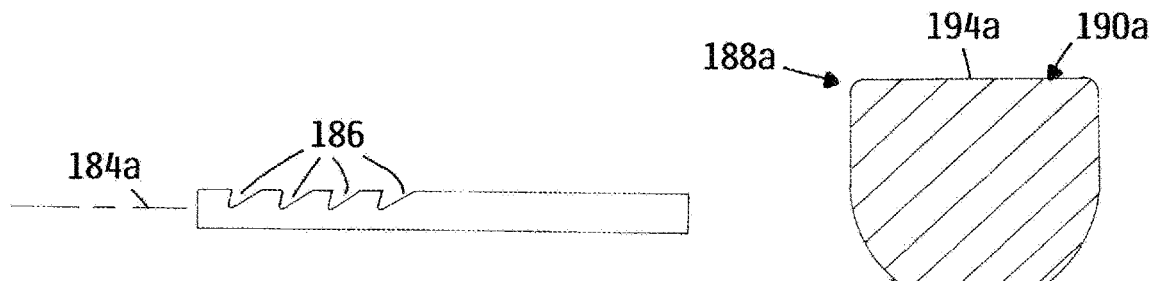
FIG. 11A is an enlarged, elevation view of a tip portion of the A/B insertion tool of FIG. 11 in an embodiment of the invention.
Figure 11B:
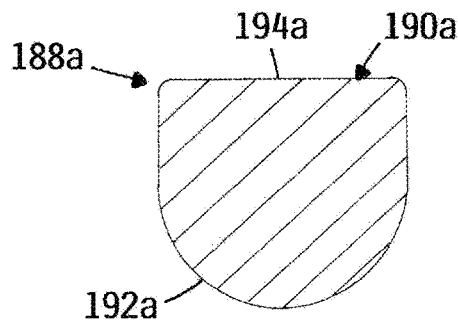
FIG. 11B is a sectional view of the "D-shaped" shaft portion of the A/B insertion tool of FIG. 11 in an embodiment of the invention.

Referring to FIGS. 11, 11A and 11B, the A/B insertion tool 36a, used to augment insertion of both the A- and B-modular segments 32a and 32b is depicted in an embodiment of the invention. The A/B insertion tool 36a includes a shaft portion 172a with a flag 174a extending from a proximal end 176a and a tip portion 178a extending from a distal end 182a.

The tip portion 178a defines a rotation axis 184a and further defines notches 186 formed on one side that are shaped and positioned complementary to the detents 156 of the mounting ports 152. In certain embodiments, the shaft portion 172a includes a cross-section 188a that has the same profile as the rail head 92 of the modular segments 32. Accordingly, when in the proper rotational orientation about the rotation axis 184a, the shaft portion 172a effectively provides a proximal extension of the rail head 92.

In the depicted embodiment, the shaft portion 172a of the A/B insertion tool 36a defines a "D-shaped" profile 190a having an arcuate portion 192a and a flat face portion 194a. The flag 174a of the A/B insertion tool 36a can be "L-shaped" as depicted in FIG. 11, with a short leg 196a of the flag 174a extending from the flat face portion 194a of the D-shaped shaft portion 172a.

Figure 12:
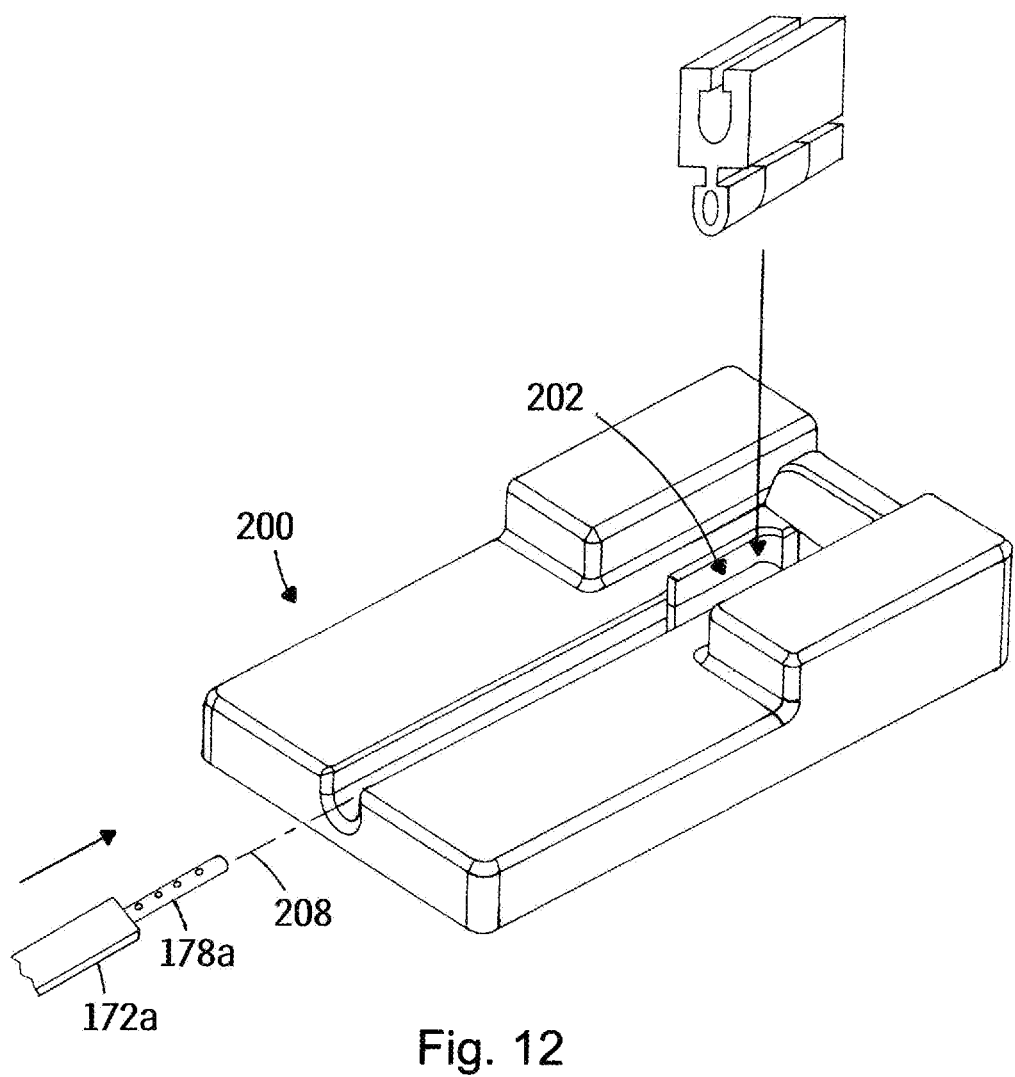
FIG. 12 is a perspective view of an assembly of an A- or B-segment/insertion tool assembly in an embodiment of the invention.
Figure 12A:
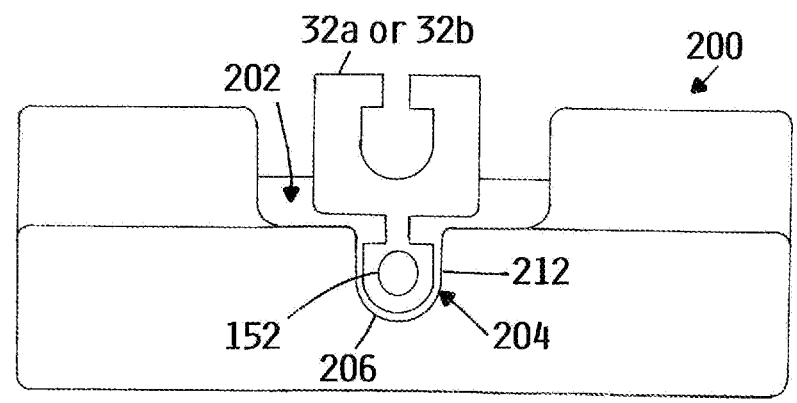
FIG. 12A is an elevational view of the assembly of FIG. 12.

Referring to FIGS. 12 and 12A, assembly of the A/B insertion tool 36a and one of the A- and B-segments 32a and 32b is depicted in an embodiment of the invention. In one embodiment, the assembly can be augmented by a segment loading platform 200. In one embodiment, the segment loading platform 200 includes a segment bay 202 that is aligned with a "U-shaped" channel 204 having an arcuate portion 206 concentric about a loading axis 208. The segment bay 202 is configured with a bottom portion 212 configured to accept and register the rail portion of the modular segment 32a or 32b. The U-shaped channel 204 is dimensioned for sliding engagement with the D-shaped profile 190a of the shaft portion 172a.

One of the A- or B-segments 32a or 32b is placed in the segment bay 202 so that the rail portion 82 of the segment 32 is properly registered within the bottom portion of the segment bay. The shaft portion 172a of the A/B insertion tool 36a is placed within the U-shaped channel 204 of the segment loading platform 200 so that the arcuate portion 192a of the D-shaped profile 190a registers against the arcuate portion 206 of the U-shaped channel 204. The registrations of the modular segment 32a or 32b and the shaft portion 172a of the A/B insertion tool 36a aligns the rotation axis 184a of the tip portion 178a and the rail axis 94a (and therefore the mounting port 152a or 152b) of the corresponding modular segment 32a or 32b.

The registrations also rotationally orient the tip portion 178a of the A/B insertion tool 36a and the mounting port 152a or 152b of the modular segment 32a or 32b so that the notches of the tip portion 178a are aligned with the detents 156a or 156b of the mounting port 152a or 152b. The tip portion 178a is slid into the mounting port 152a or 152b until each of the plurality of detents 156a or 156b of the mounting port 152a or 152b occupies a corresponding one of the notches 186a on the tip portion 178a.

It is noted that the C-segment 32c does not include a mounting rail, and therefore cannot include a mounting port that is concentric with a rail portion. Accordingly, the C-segment includes a mounting port 152c formed in the body portion 84c, the mounting port 152c defining an axis 214 that is parallel with and on the same transverse plane 72c as the slot axis 116c and having the same aspects as the mounting ports 152a and 152b of the A- and B-segments 32a and 32b.

Referring to FIGS. 13A through 13H, an assembly sequence is depicted for the three-segment prosthesis 34b of FIG. 2B. An A-segment/insertion tool assembly 220a comprising the A-segment 32a and the A/B insertion tool 36a is first placed in an evacuated disc nucleus space (FIG. 13A; evacuated disc nucleus space not depicted). A B-segment/insertion tool assembly 220b comprising the B-segment 32b and another A/B insertion tool 36b is then slid over a proximal end 222a of the A-segment/insertion tool assembly 220a and translated along the shaft 172a of the A/B insertion tool 36a of the A-segment/insertion tool assembly 220a (FIG. 13B).

During this step, the open side 128b of the elongate slot 112b of the B-segment 32b is aligned to pass over the short leg 196a of the L-shaped flag 174a of the A-segment insertion tool 36a of the A-segment/insertion tool assembly 220a, which also places the elongate slot 112b of the B-segment 32b in proper orientation for translation along the D-shaped shaft 172a of the A/B insertion tool 36b of the B-segment/insertion tool assembly 220b.

The B-segment 32b is then slid over the rail portion 82a of the A-segment 32a until the B-segment 32b registers against the stop portion 98a of the A-segment 32a (FIG. 13C). The open side 128b of the elongate slot 112b slides over the web 88b of the rail portion 82b, the open side 128b having been properly aligned when slid over the short leg 196a of the L-shaped flag 174a. The user can determine that the B-segment 32b is in place when the flags 174a and 174b of the A/B insertion tools 36a and 36b of the A- and B-segment insertion tool assemblies 220a and 220b are aligned.

Upon registration of the B-segment 32b against the stop portion 98a of the A-segment 32a, the barb portions 96a on the rail portion 82a of the A-segment 32a should be registered within the recesses 118b of the B-segment 32b. However, the user can tug the B-segment/insertion tool assembly 220b in the proximal direction relative to the A-segment/insertion tool assembly 220a to assure that the barb portions 96a are set within the recesses 118b.

The A/B insertion tool 36a of the A-segment/insertion tool assembly 220a is then removed. Removal is accomplished by rotation of the A/B insertion tool 36a of the A-segment/insertion tool assembly 220a 180° about the rotation axis 184a (FIG. 13D). This action causes the notches 186a of the tip portion 178a of the A/B insertion tool 36a of the A-segment/insertion tool assembly 220a to rotate away from the detents 156a in the mounting port of the A-segment 32a, thus enabling the A/B insertion tool 36a of the A-segment/insertion tool assembly 220a to be removed from the mounting port 156a with reduced interference from the detents 156a. The A/B insertion tool 36a of the A-segment/insertion tool assembly 220a is then removed from the mounting port 152a, leaving only the A- and B-segments 32a and 32b coupled to the B-segment/insertion tool assembly 220b (FIG. 13E).

A C-segment/insertion tool assembly 220c comprising the C-segment 32c and the C insertion tool 36c is then aligned so that the slot portion 112c of the C-segment 32c is slid over a proximal end 222b of the B-segment/insertion tool assembly 220b, and the C-segment/insertion tool assembly 220b being translated along the shaft 172b of the insertion tool 36b of the B-segment/insertion tool assembly 220b (FIG. 13F).

The C insertion tool 36c is described in more detail below in the discussion attendant to FIG. 19. The C-segment 32c is then slid over the rail portion 82b of the B-segment 32b until the C-segment 32c registers against the stop portion 98b of the B-segment 32b (FIG. 13G). The insertion tool 36b of the B-segment/insertion tool assembly 220b is then removed (FIG. 13H). The steps depicted at FIGS. 13F through 13H are conducted in the same manner as the steps depicted at FIGS. 13B through 13E.

The insertion tool of the C-segment/insertion tool 36c is removed by rotating the insertion tool 36c 180° (FIG. 13H) and removing it from the mounting port 152c, thereby leaving the prosthesis fully assembled an in place (FIG. 2B).

In certain embodiments, supplemental tools can be included and utilized in for enhanced manipulation of the modular segments. The supplemental tools are of particular utility when handling modular segments that are of a homogeneous, compliant material. The supplemental tools can include the removal tool 44, the A-segment stabilizer 46, the B-segment stabilizer 48 and the C-segment stabilizer 52 (FIG. 1).

Figure 14:
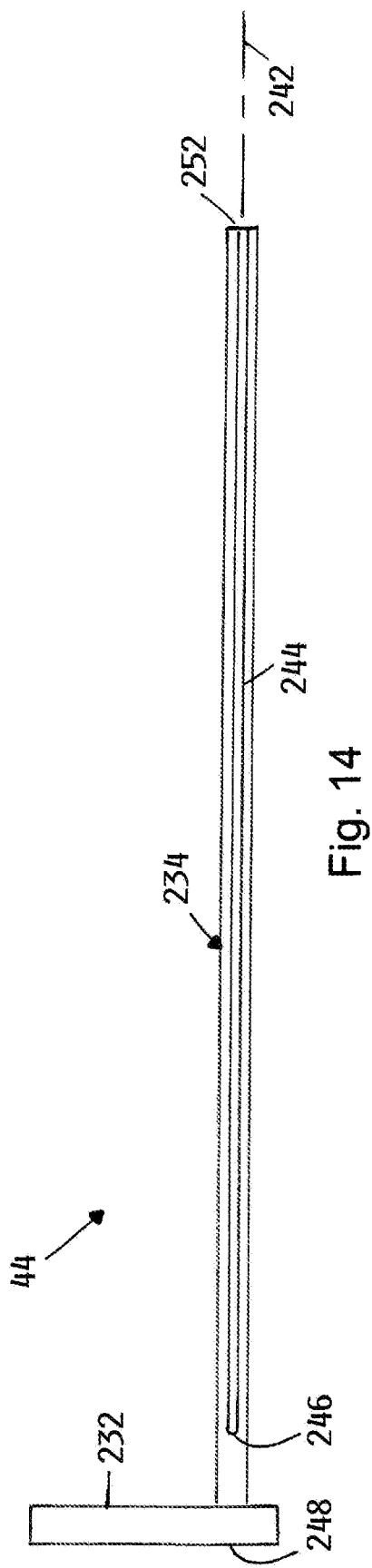
FIG. 14 is a side view of a removal tool in an embodiment of the invention.
Figure 14A:
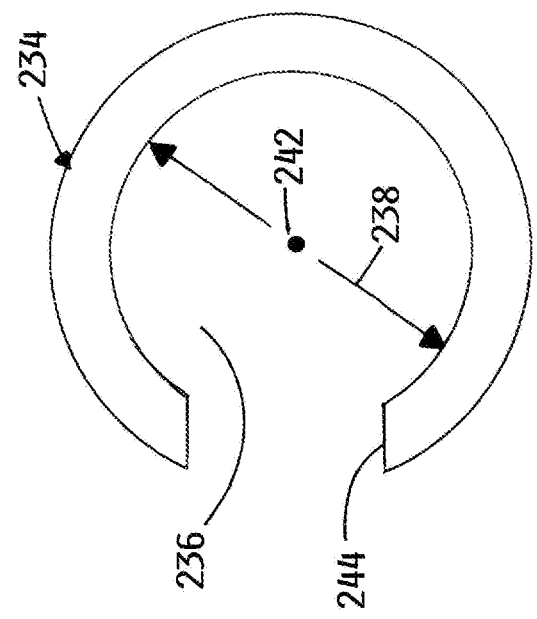
FIG. 14A is a sectional view of the removal tool of FIG. 14.
Figure 16:
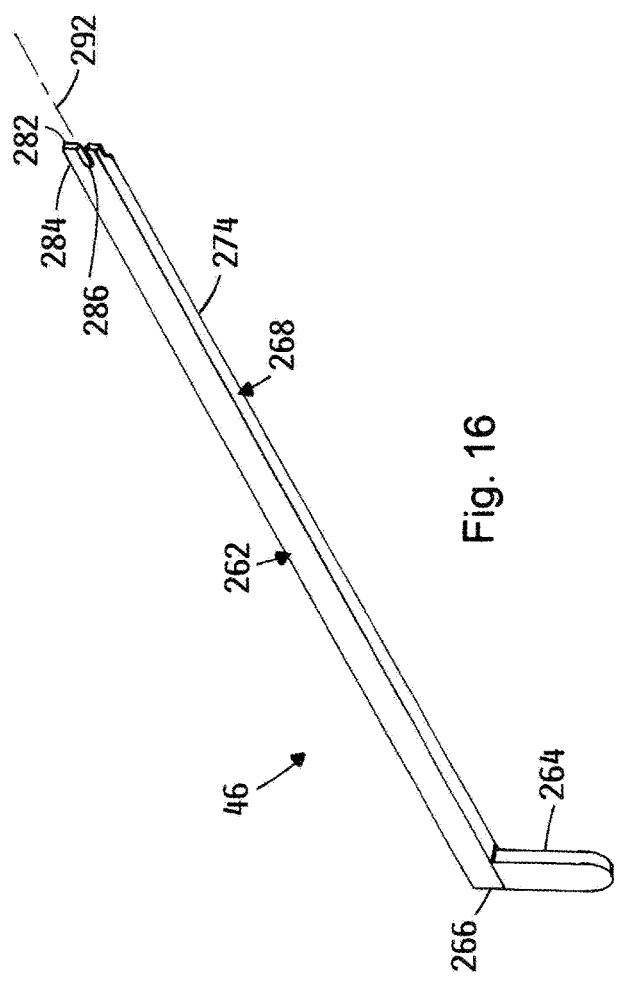
FIG. 16 is a perspective view of an A-segment stabilizer in an embodiment of the invention.
Figure 16A:
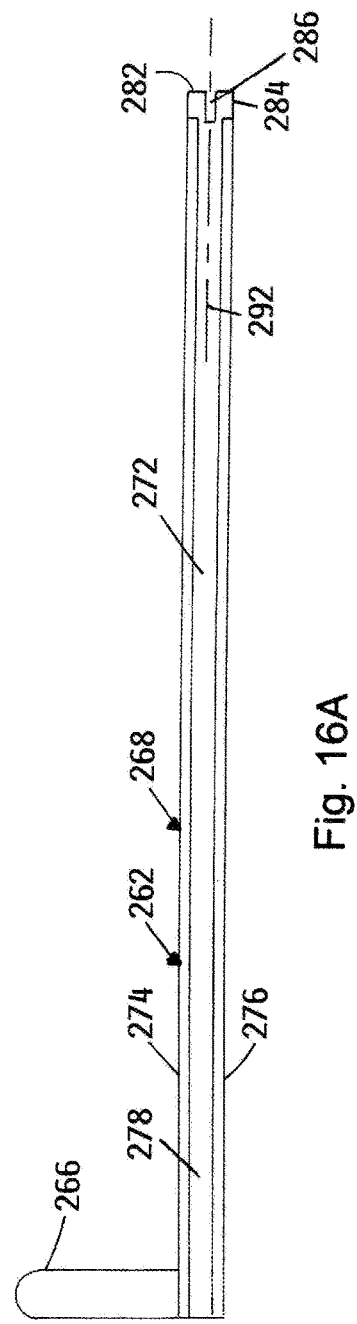
FIG. 16A is a side view of the A-segment stabilizer of FIG. 16 in an embodiment of the invention.

Referring to FIGS. 14 and 14A, the removal tool 44 is depicted in an embodiment of the invention. The removal tool 44 includes a handle portion 232 and a shaft portion 234. The shaft portion 234 defines a bore 236 having an inner diameter 238 concentric about a central axis 242. The inner diameter 238 of the bore 236 is dimensioned large enough to slide over the D-shaped profile 190a or 190b of the A- and B-segment insertion tool 36a or 36b, as well as the round profile of the C-segment insertion tool 36c. The removal tool 44 includes a slot 244 on one side thereof, the slot 244 extending on one side of the removal tool and from a location 246 proximate a proximal end 248 of the removal tool 44 through a distal end 252 of the removal tool 44.

Referring to FIGS. 15A through 15D, operation of the removal tool 44 is depicted in an embodiment of the invention. Typically after the insertion tool has been rotated 180° to disengage the detents 156 and notches 186 (FIGS. 15A and 15B), the central axis 242 of the removal tool 44 is aligned with the rotation axis 184 of the insertion tool 36 and slid over the proximal end 176 of the insertion tool 36, the slot 244 being aligned to pass over the short leg 196 of the L-shaped flag 174.

The shaft portion 234 of the removal tool 44 is slid over the shaft portion 172 of the insertion tool 36 until the distal end 252 of the removal tool 44 is brought into contact with the modular segment 32 (FIG. 15C). The insertion tool 44 is then pulled out of the mounting port 152 by application of a clamping force F between the flag portion 174 of the insertion tool 36 and the handle portion 232 of the removal tool 44 (FIG. 15D). The operator typically applies the clamping force F by squeezing the flag portion 174 and the handle portion 232 between the index finger and the thumb or palm of the hand.

Functionally, while the act of rotating a given insertion tool 36 180° makes removal of the insertion tool 36 from the mounting port 152 easier, the friction between the tip portion 178 of the insertion tool 36 and the modular segment 32 can still be substantial, in part because the detents 156 are compressed against the cylindrical surface of the tip portion 178 after the 180° rotation. The removal tool 44 provides a controlled, mechanically leveraged way to remove insertion tools 36 in situ while maintaining a low profile.

Referring to FIGS. 16, 16A, 17, 17A and 17B, the A- and B-segment stabilizers 46 and 48 are depicted in embodiments of the invention. The A- and B-segment stabilizers 46 and 48 include many common aspects, which are indicated in the figures with like-numbered numerical references. The A-stabilizer 46 includes a shaft portion 262 having a handle 264 attached at a proximal end 266. The shaft portion 262 includes what is effectively a channel structure 268 defining a channel 272 on one side thereof, the channel structure 268 including opposed flanges 274 and 276 separated by a flat portion 278.

The channel 272 thus defined is dimensioned to enable insertion tools 36 to slidably translate therein, with the flat portion 278 of the D-shaped shaft 172 engaged with the flat portion 278 of the A-segment stabilizer 46. At a distal end 282, the flat portion 278 includes an extension portion 284 that extends beyond the opposed flanges 274, 276, the extension portion 284 including a slot 286 formed thereon. The slot 286 is formed along an elongate axis 292 and is accessible from the distal end 282.

The B-segment stabilizer 48 also includes the channel structure 268 extending from the proximal end 266 to near the distal end 282. At the proximal end 266, the B-segment stabilizer includes a ramp portion 294 formed within the channel 272. In the absence of a handle, the B-segment stabilizer includes a grip portion 296 formed on the proximal end 266. Near the distal end 282, the B-segment stabilizer 48 includes an additional guide structure 302 that effectively defines an asymmetric H-beam profile 304.

The channel structure 272 and guide 302 structure define the channel 272 continuously along the length of the B-segment stabilizer 48. The guide structure 302 includes opposed flanges 274 and 276 that extend normal to the flat portion 278 in both directions. The guide structure 302 also includes opposed lip portions 306 that extend toward each other to define a gap 308 therebetween.

Figure 18B:
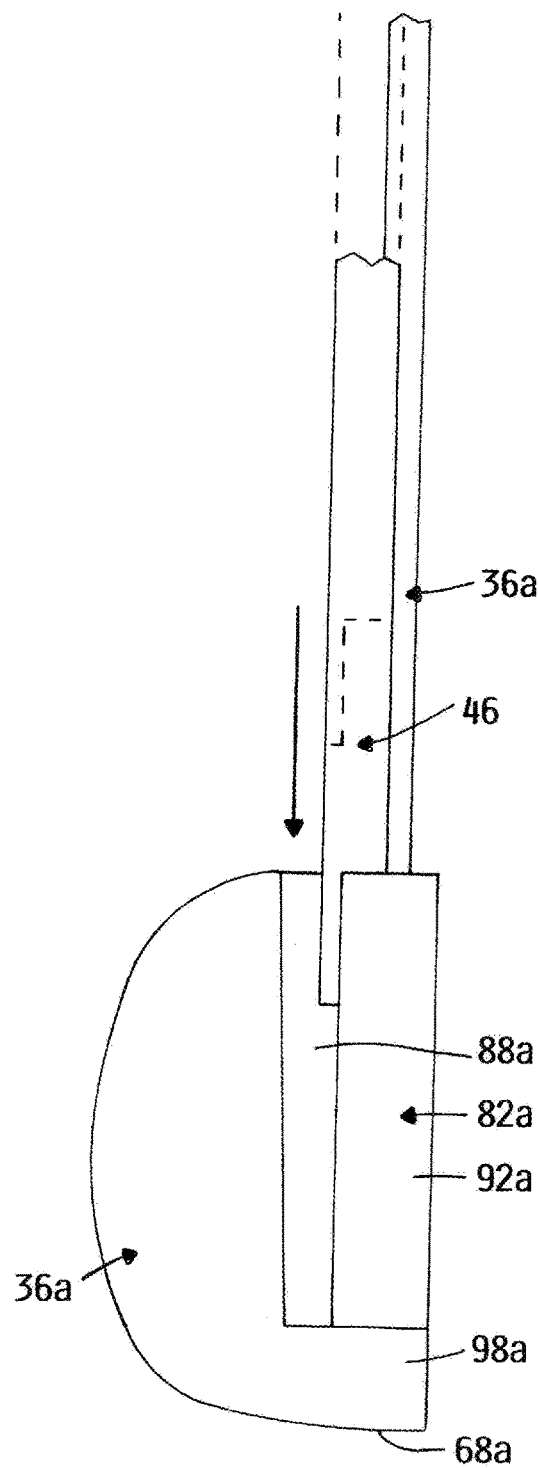

Referring to FIGS. 18A and 18B, operation of the A-segment stabilizer 46 is depicted in an embodiment of the invention. Prior to insertion of the A-segment 32a into the evacuated disc nucleus space, the A-segment/insertion tool assembly 220a is loaded into the channel 272 of the A-segment stabilizer 46 (FIG. 18A). After or simultaneously with the loading, the A-segment stabilizer 46 is translated toward the A-segment 32a until the web 88a of the rail portion 82a registers within the slot 286 (FIG. 18B).

For the B-segment stabilizer 48, the guide structure 302 is slid over the distal end 176a of the A insertion tool 36a to capture the D-shaped shaft portion 172a of the A insertion tool 36a (shown in phantom in FIG. 17A) between the flange portions 274, 276 and lip portions 306 of the guide structure 302 of the B-segment stabilizer 48. The channel 272 of the B-segment stabilizer 48 is translated over the B-segment/insertion tool assembly 220b until the web 88b of the rail portion 82b is registered in the slot 286. In the depicted embodiment, the B-segment stabilizer 48 does not include a handle akin to the A-segment stabilizer 46 because such a handle would create clutter and interference amongst the flags 178a and 178b of the A- and B-insertion tools 36a and 36b. In this way, additional guidance and control for coupling the B-segment 32b to the A-segment 32a is provided in situ.

The ramp portion 294 guides the flags 174a and 174b at the proximal ends of the insertion tools 36a and 36b away from each other during assembly of the prosthesis 34. This prevents the flag 174b of the A/B insertion tool 36B from catching on the flag 174a of the adjacent A/B insertion tool 36a. Removal of the A- and B-segment stabilizers 46 and 48 is accomplished by disengaging them from the web 88a, 88b of the respective rail portion 82a, 82b in the proximal direction.

Referring to FIGS. 19, 19A and 19B (referred to collectively as FIG. 19), the C insertion tool 36c is depicted in an embodiment of the invention. The C insertion tool 36c includes a shaft portion 172c having a tip portion 178c at a distal end 182c and a flag portion 174c at a proximal end 176c. In one embodiment, the flag portion 174c extends in an opposite direction from the flag portions 174a, 174b of the A/B insertion tools 36a, 36b.

The tip portion 178c defines a tip portion axis 310. The notch aspects 186c of the tip portion 178c for the C insertion tool 36c can be the same as for the A/B insertion tool 36a. The shaft portion 172c of the C insertion tool 36c is essentially cylindrical about a cylindrical axis 312. In the depicted embodiment, the cylindrical axis 312 of the shaft portion 172c and the tip portion axis 310 of the tip portion 178c are eccentric (FIGS. 19A and 19B).

Referring to FIGS. 20, 20A and 20B, the C-segment stabilizer 52 is depicted in an embodiment of the invention. The C-segment stabilizer 52 includes a hollow shaft portion 322 having a handle 324 on a proximal end 326 and a guide structure 328 near a distal end 332. The hollow shaft portion 322 includes structure defining a slot 334 extending on a first side 336 of thereof and from a location 338 proximate the proximal end 326 and through the distal end 332 of the C-segment stabilizer 52.

The guide structure 328 comprises two opposing flanges 342 and 344 that extend from a second side 346 of the hollow shaft portion 322, the second side 346 being opposite the first side 336. The opposing flanges 342, 344 each include lip portions 352 that extend toward each other to define a gap 356 therebetween. The A/B insertion tool 36b and the C insertion tool 36c are depicted in phantom in FIG. 20B.

In operation, the hollow shaft portion 322 of the C-segment stabilizer 52 is aligned with the cylindrical axis 312 of the C insertion tool 36c and with the slot 334 aligned to pass over the flag portion 174c. The C-segment stabilizer 52 is then translated over the C insertion tool 36c until the distal end 332 engages the C-segment 32c.

Functionally, the guide structure 328 captures the D-shaped shaft 172c of the adjacent A/B insertion tool 36b between the flanges 324 and 344 of the guide structure 328, to further assist the user in guiding the B-segment 32b into the evacuated disc nucleus space. The slot 334 of the C-segment stabilizer enables passage of the hollow shaft portion 322 over the shaft flag portion 174c of the C insertion tool 36c. Likewise, the gap 356 enables passage of the guide structure 328 over the flag portion 174b of the A/B insertion tool 36b.

The inner diameter of the hollow shaft 322 is dimensioned so that the A/B insertion tool 36b cannot be inserted in the C-segment stabilizer. Thus, the round hollow shaft 322 of the C-segment stabilizer 52 serves as a key to prevent insertion of the AB insertion tool 36a therein. The eccentricity of the tip portion 178c relative to the shaft portion 172c allows room for the structure of the hollow shaft portion 322 between the insertion tools 36b and 36c. The distal end 332 of the C-segment stabilizer 52 provides a bearing surface that spreads the force of the insertion operation over a larger area, thus preventing deformation of the C-segment 32c during insertion of the C-segment 32c.

A purpose of the A-, B-, and C-segment stabilizers 46, 48 and 52 generally is to enable manipulation the respective A-, B- and C-segments 32a, 32b and 32c during implantation, as well as maneuvering the prosthesis 34 within the evacuated disc nucleus space while the prosthesis 34 is at various stages of assembly. The stabilizers 46, 48, 52 reduce the risk of the tip portion 178 of the various insertion tools 36 becoming dislodged from the respective mounting port 152 during positioning of the partially or fully assembled prosthesis 34.

In certain embodiments, various of the components discussed above are included as a kit. The kit can include some or all of the components presented in FIG. 1. The kit can also include operating instructions on a tangible medium such as a paper document, a compact disc (CD), a digital video disc (DVD), or a central computer accessed, for example, over the interne. The operating instructions can include various of the instructions and sequences described above.

Figure 21:
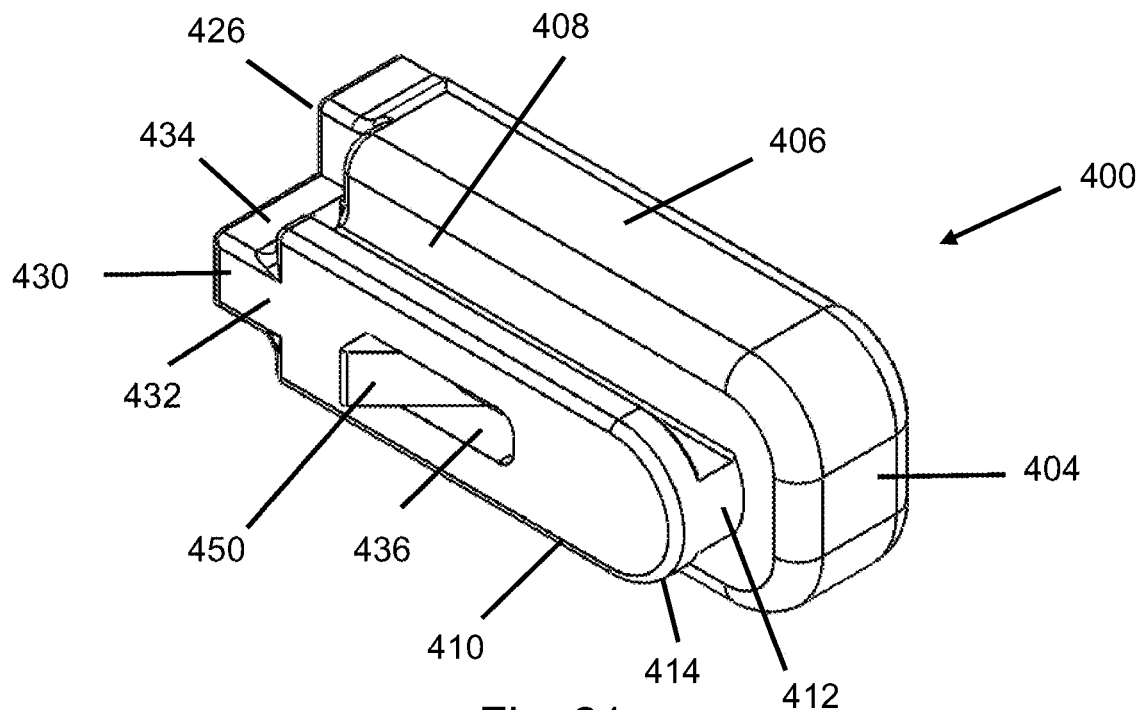
FIG. 21 is a perspective view of the semi-rigid surgical implant.
Figure 23:
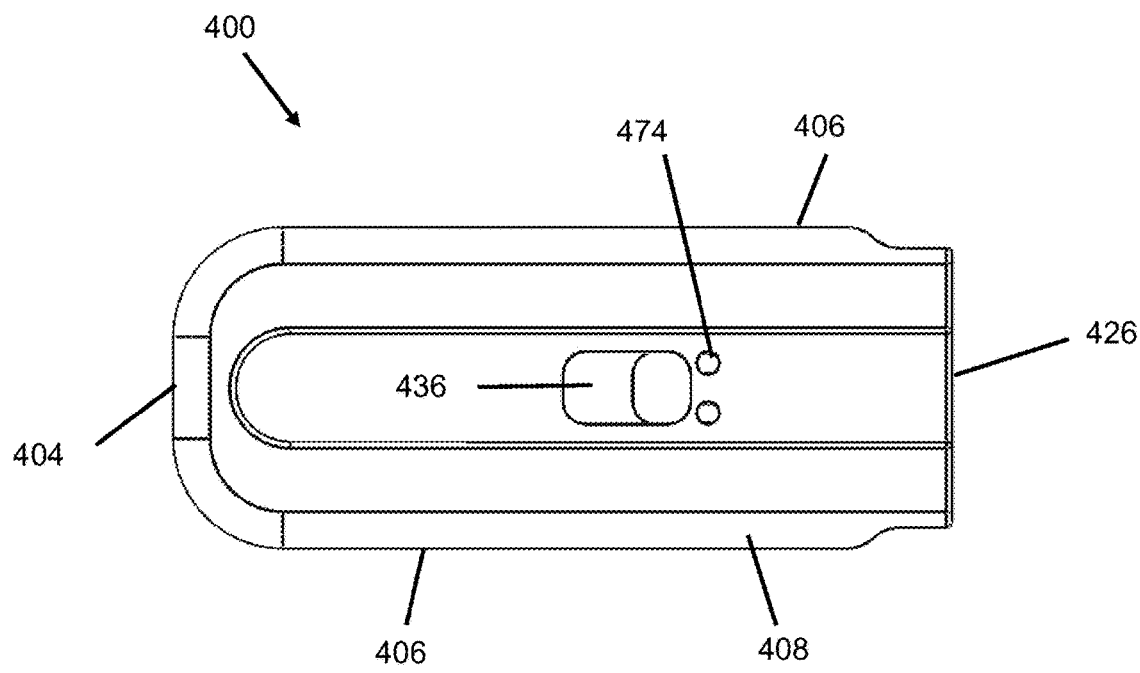
FIG. 23 is a top view of the semi-rigid surgical implant of FIG. 21.
Figure 24:
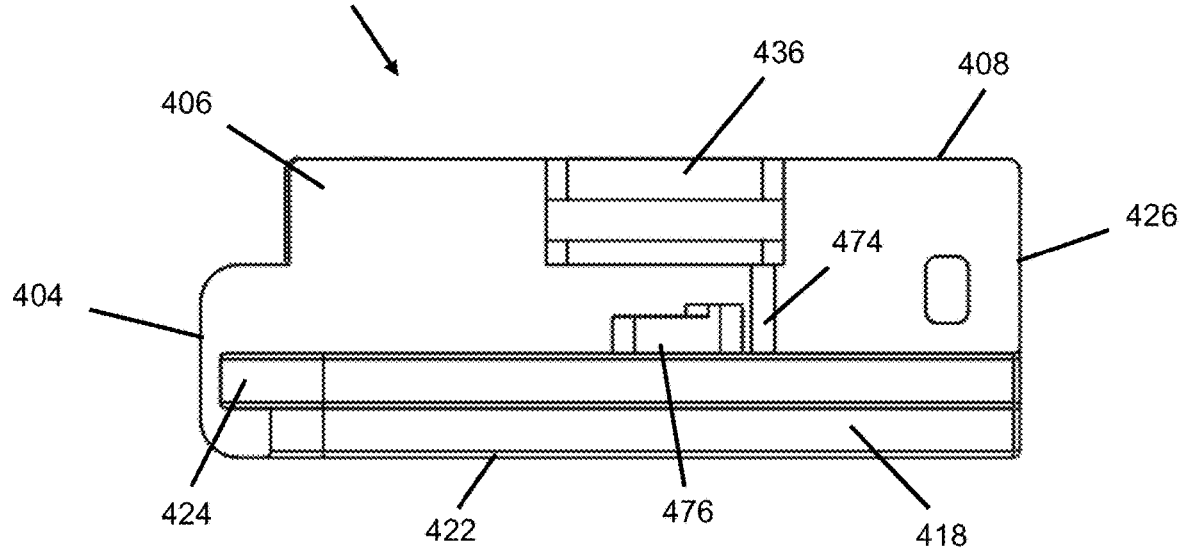
FIG. 24 is a side view of the semi-rigid surgical implant of FIG. 21.

An embodiment of the semi-rigid surgical implant 400 is illustrated in FIGS. 21, 23 and 24. In certain embodiments, the semi-rigid surgical implant 400 has an elongated configuration.

A front surface 404 of the semi-rigid surgical implant 400 may have curved regions along upper, lower and side edges thereof to minimize the potential of the semi-rigid surgical implant 400 cutting or otherwise damaging tissue as the semi-rigid surgical implant 400 is inserted.

Similarly, side surfaces 406 may have curved regions along upper and lower edges thereof to minimize the potential of the semi-rigid surgical implant 400 cutting or otherwise damaging tissue as the semi-rigid surgical implant 400 is inserted.

A male engagement section 410 extends from an upper surface 408 of the semi-rigid surgical implant 400. In certain embodiments, the male engagement section 410 generally includes a base engagement section 412 and an extension engagement section 414.

The base engagement section 412 is attached to semi-rigid surgical implant 400 and extends from the upper surface 408. The extension engagement section 414 is attached to a side of the base engagement section 412 that is opposite the semi-rigid surgical implant 400. In certain embodiments, the extension engagement section 414 is oriented generally perpendicular to the base engagement section 412.

The extension engagement section 414 has a width that is greater than a width of the base engagement section 412. An end of the extension engagement section 414 that is oriented towards the front surface 404 may be curved to minimize the potential of the male extension section 410 cutting or otherwise damaging tissue as the semi-rigid surgical implant 400 is inserted.

A female engagement section 420 is formed in a lower surface 418 as illustrated in FIG. 24. In certain embodiments, the female engagement section 420 generally includes a first channel section 422 and a second channel section 424.

The first channel section 422 extends into the lower surface 418. The first channel section 422 has a width that is slightly larger than the width of the base engagement section 412. The first channel section 422 is closed proximate the front surface 404 and is open proximate a back surface 426.

The second channel section 424 is formed in the semi-rigid surgical implant 400 at an end of the first channel section 422 that is opposite the lower surface 418. The second channel section 424 has a width that is slightly larger than the width of the extension engagement section 414. The second channel section 424 is closed proximate the front surface 404 and is open proximate the back surface 426.

The configuration of the male engagement section 410 and the female engagement section 420 enables adjacent semi-rigid surgical implants 400 to slide into engagement with each other.

Proximate the back surface 426, the semi-rigid surgical implant 400 includes a surgical instrument engagement region 430 to facilitate engagement of the semi-rigid surgical implant 400 with the surgical implant inserter 500.

In certain embodiments, the surgical instrument engagement region 430 may include a central region 432 and a two tab regions 434. The central region 432 extends from the back surface 426. The tab regions 434 extend from the central region 432 proximate an end thereof that is opposite the semi-rigid surgical implant 400. In certain embodiments, the tab regions 434 extend from opposite sides of the central region 432. In certain embodiments, the tab regions 434 are oriented generally perpendicular to the central region 432.

Intermediate the side surfaces 406, an opening 436 is formed in the upper surface 408. In certain embodiments, the opening 436 extends through the lower surface 418 as illustrated in FIG. 23. The opening 436 is adapted to receive at least a portion of the locking mechanism 450 as is described in more detail herein.

Figure 22:
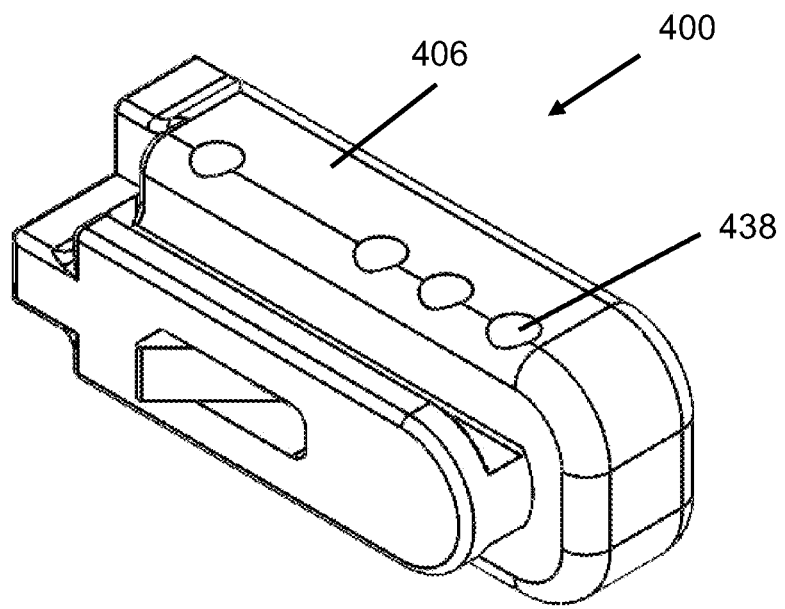
FIG. 22 is a perspective view of an alternative embodiment of the semi-rigid surgical implant.

In an alternative embodiment of the semi-rigid surgical implant 400, which is illustrated in FIG. 22, the semi-rigid surgical implant 400 includes at least one aperture 438 in a side thereof. In certain embodiments, each of the apertures 438 extend between opposite side surfaces 406. The apertures 438 may be oriented generally perpendicular to the side surfaces 406.

Figure 25:
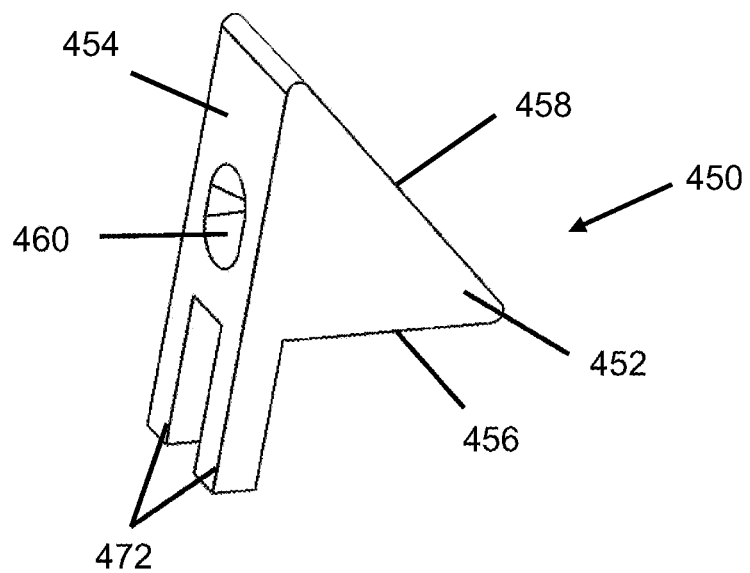
FIG. 25 is a perspective view of a locking mechanism for the semi-rigid surgical implant of FIG. 26.
Figures 26, 27:
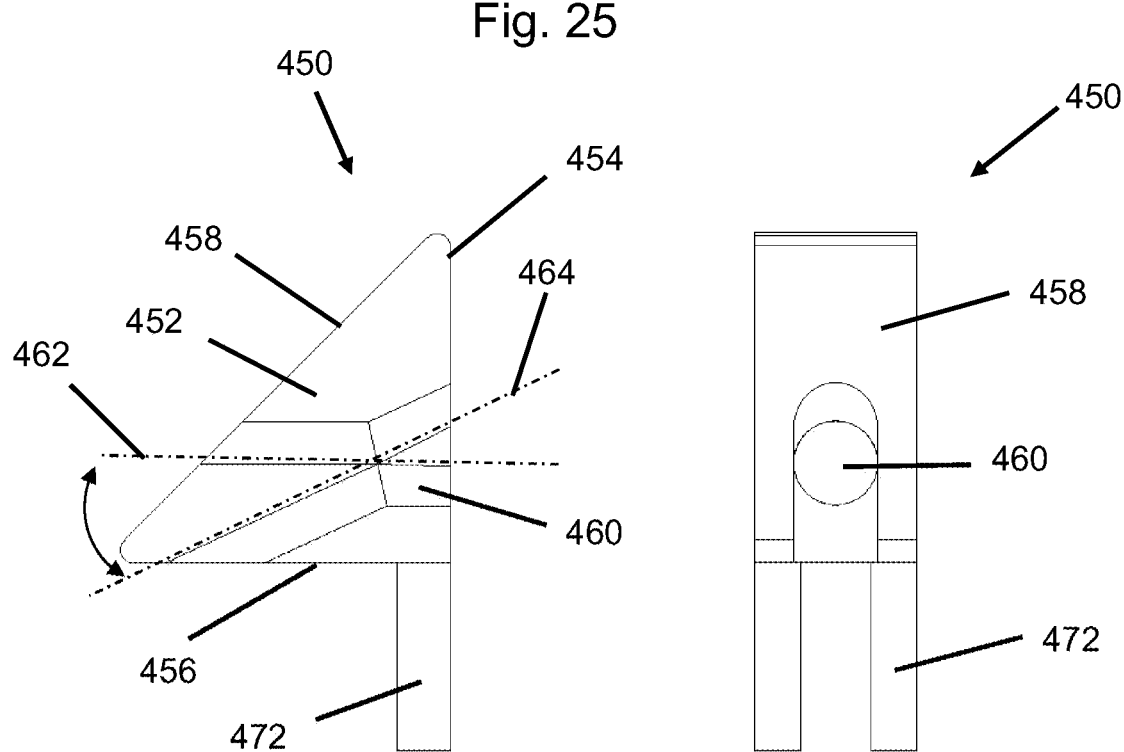
FIG. 26 is a side view of the locking mechanism of FIG. 25.
FIG. 27 is a front view of the locking mechanism of FIG. 25.

The locking mechanism 450 includes a main section 452, as illustrated in FIGS. 25-27. The main section 452 may have a generally triangular shape that includes a first side 454, a second side 456 and a third side 458. In certain embodiments, the first side 454 is generally perpendicular to the second side 456 and a length of the first side 454 is approximately equal to a length of the second side 456.

Figure 29:
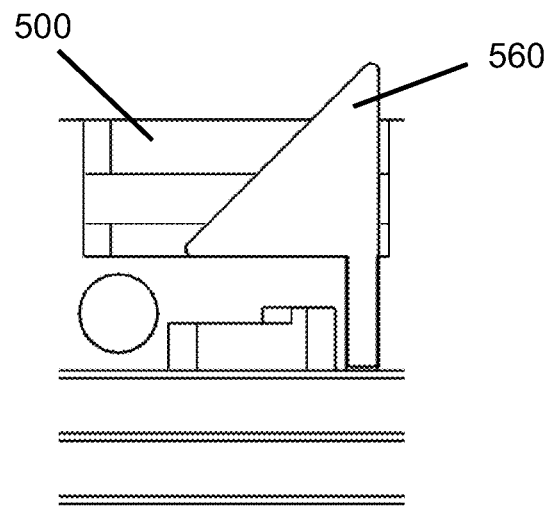
FIG. 29 is a side view of the locking mechanism in an undeflected configuration.

When the locking mechanism 450 is in an undeflected configuration, the first side 454 is oriented generally perpendicular to the upper surface 408 and the second side 454 is oriented generally parallel to the upper surface 408 as illustrated in FIG. 29.

The main section 452 has an aperture 460 extending therethrough as most clearly illustrated in FIG. 26. In certain embodiments, the aperture 460 is wider proximate opposite ends thereof than intermediate opposite ends thereof. The aperture 460 is defined by a first line 462 and a second line 464.

In certain embodiments, the first line 462 is generally parallel to the second side 454 and the second line 464 is oriented at an angle of between about 10 degrees and about 40 degrees with respect to the first line 462. The aperture 460 thereby permits the locking mechanism 450 to pivot with respect to the semi-rigid surgical implant 400.

At the smallest part of the aperture 460, the aperture 460 has a generally circular profile with a diameter that is slightly larger than a diameter of a locking pin 470 such that the locking pin 470 is extendable through the aperture 460 to retain the locking mechanism 450 in engagement with the semi-rigid surgical implant 400.

The main section 452 has two legs 472 extending from the second side 456. The legs 472 may be oriented in substantially alignment with the first side 454. The legs 472 extend into mounting apertures 474 in the semi-rigid surgical implant 400.

Figure 28:
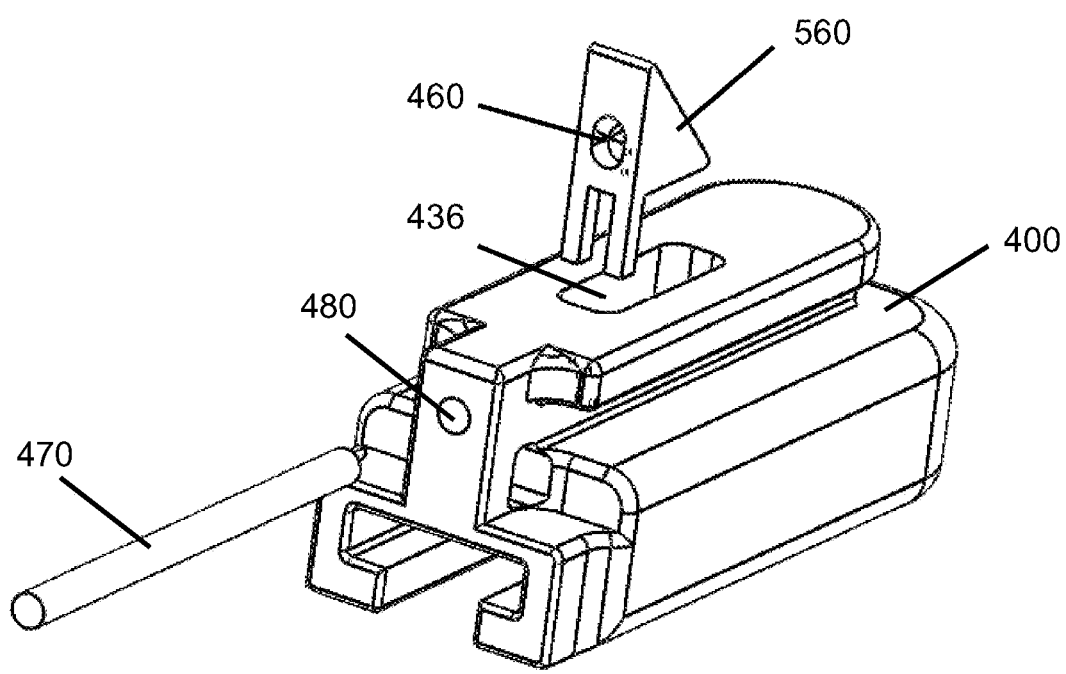
FIG. 28 is an exploded view of the semi-rigid surgical implant.

The semi-rigid surgical implant 400 is assembly by extending the locking mechanism 450 into the opening 436 and then extending the locking pin 470 into an aperture 480 in the back surface 426 until the locking pin 470 extends through the aperture 460 to operably attach the locking mechanism 450 to the semi-rigid surgical implant 400. FIG. 28 is an exploded view of the locking mechanism 450, the locking pin 470 and the semi-rigid surgical implant 400.

The locking pin 470 thereby acts as a pivot point that permits the locking mechanism 450 to pivot between the undeflected configuration and the deflected configuration. In certain embodiments, at least a portion of the locking mechanism 450 deforms when the locking mechanism 450 moves from the undeflected configuration to the deflected configuration. The deformation process redistributes energy.

Figure 30:
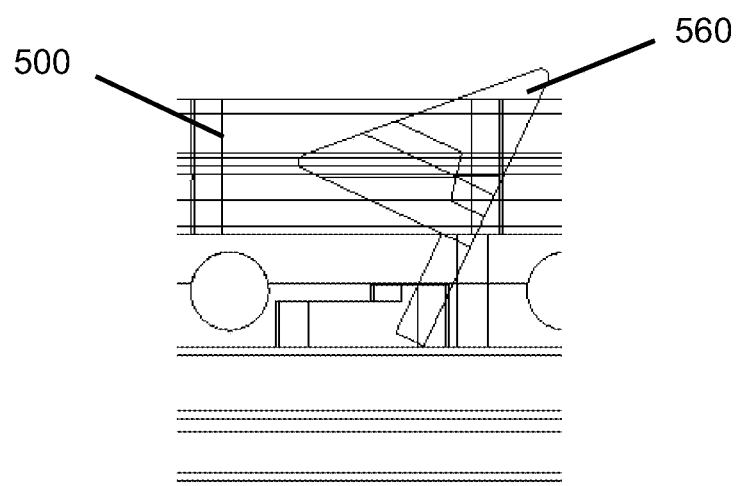
FIG. 30 is a side view of the locking mechanism in a deflected configuration.
Figure 31:
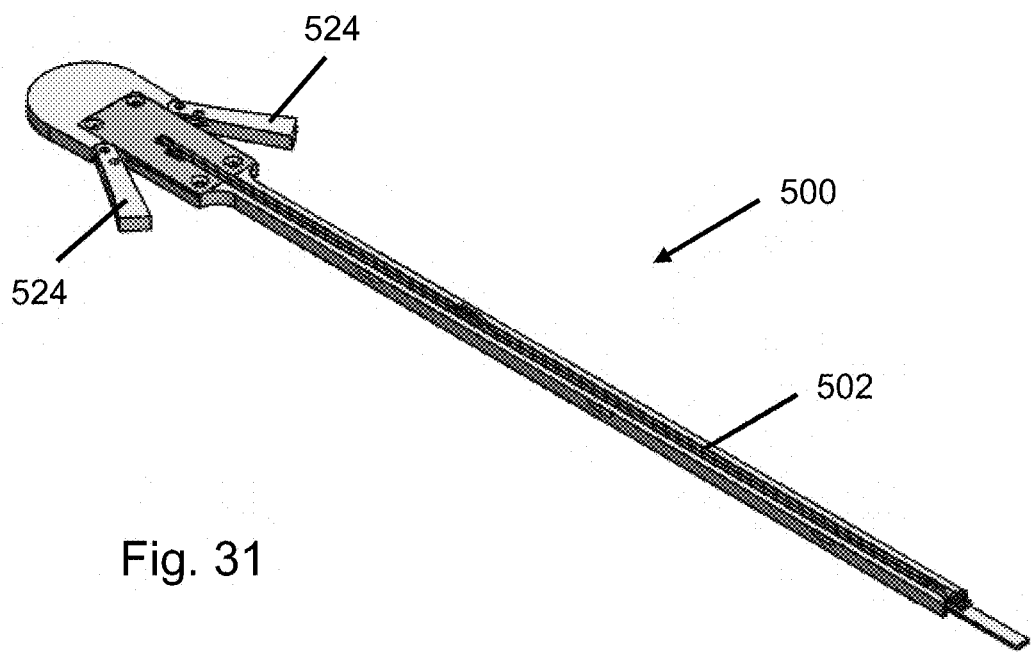
FIG. 31 is a perspective view of a surgical instrument for handling a semi-rigid surgical implant.
Figure 32:
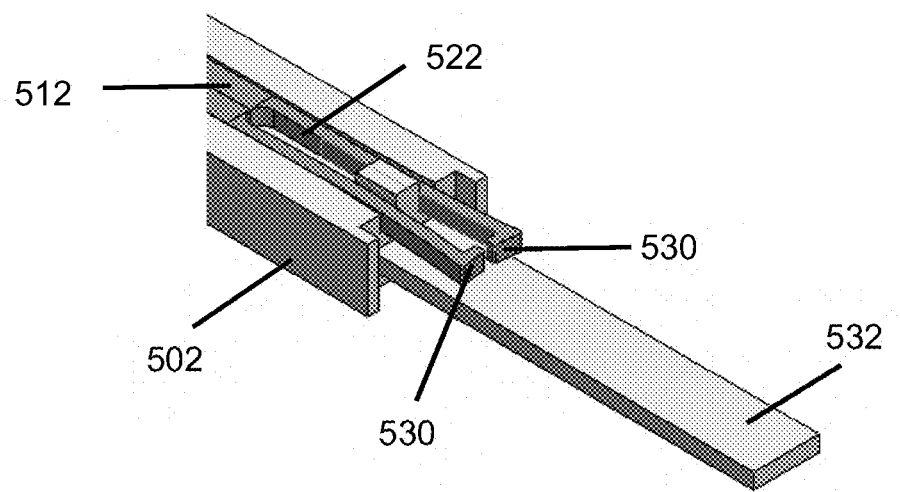
FIG. 32 is an enlarged perspective view of a distal end of the surgical instrument illustrated in FIG. 31.

FIG. 29 illustrates the locking mechanism 450 in an undeflected configuration with respect to the semi-rigid surgical implant 400. FIG. 30 illustrates the locking mechanism 450 in a deflected configuration with respect to the semi-rigid surgical implant 400. The locking mechanism 450 is urged from the undeflected configuration to the deflected configuration as two of the semi-rigid surgical implants 400 are slid with respect to each other during the process of attaching the two semi-rigid surgical implants 400 as described in more detail herein.

The semi-rigid surgical implant 400 may be formed from various materials using the concepts of the invention. Dimensions such as overall length, width, diameter, circumference, and other similar measurements, including shape, are expressly adaptable to the surgical use setting for which a surgical instrument of the present invention may be used.

As used herein, semi-rigid means a soft or compliant material having a relatively low hardness. A non-limiting example of a soft or compliant material is a polymer such a biocompatible polyurethane. A non-limiting example of a hardness of a soft or compliant material is a material with a durometer hardness ranging from about Shore 18 A to about Shore 55D. A further and non-limiting example of a soft or compliant material is a material with a compressive modulus between about 2 and about 100 MPa. In a preferred embodiment, the compressive modulus is between about 6 and about 20 MPa.

The surgical implant inserter 500 is adapted to removably secure the semi-rigid surgical implant 400 for implantation in a body. The surgical implant inserter 500 generally includes a shaft 502 having a proximal end and distal end. The shaft 502 has at least one channel 510 that extend from the proximal end to the distal end.

The channel 510 is adapted to receive an accessory shaft 512 having a proximal end and a distal end. The accessory shaft 512 is slidably mounted with respect to the shaft 502.

An actuation mechanism is attached to the proximal end of the accessory shaft 512. The actuation mechanism is capable of causing the accessory shaft 512 to slide with respect to the shaft 502. In certain embodiments where there is more than one accessory shaft 512, the actuation mechanism may cause the accessory shafts 512 to be actuated in unison or the actuation mechanism may permit the accessory shafts 512 to be actuated independently.

The actuation mechanism may include at least one arm 524 that is operably mounted with respect to the shaft 502. In certain embodiments, the actuation mechanism includes two arms 524 that are pivotally mounted with respect to the shaft 502.

The arms 524 may be biased to an open configuration. When the arms 524 are in the open configuration, the semi-rigid surgical implant 400 is retained in engagement with the surgical implant inserter 500. When the arms 524 are moved to a closed configuration, the semi-rigid surgical implant 400 is released from the surgical implant inserter 500.

As an alternative to manually operating the accessory shaft 512 as illustrated, the accessory shaft 512 may be remotely operated such as by attachment to a surgical robot (not shown).

An implant engagement mechanism 522 is attached to the distal end of the accessory shaft 512. The implant engagement mechanism 522 may include two inwardly directed tabs 530. When the actuation mechanism has been actuated, the inwardly directed tabs 530 are urged towards each other to engage the tab regions 434 to thereby retain the semi-rigid surgical implant 400 in engagement with the surgical implant inserter 500.

To retain the semi-rigid surgical implant 400 in an alignment that is generally parallel to the shaft 502 when the semi-rigid surgical implant 400 is attached to the surgical implant inserter 500, an extension 532 may extend from the distal end of the shaft 502.

In certain embodiments, the extension 532 may have a length that is similar to but less than the length of the semi-rigid surgical implant 400 and the extension 532 may have a width that is similar to but less than the width of the semi-rigid surgical implant 400.

Figure 33:
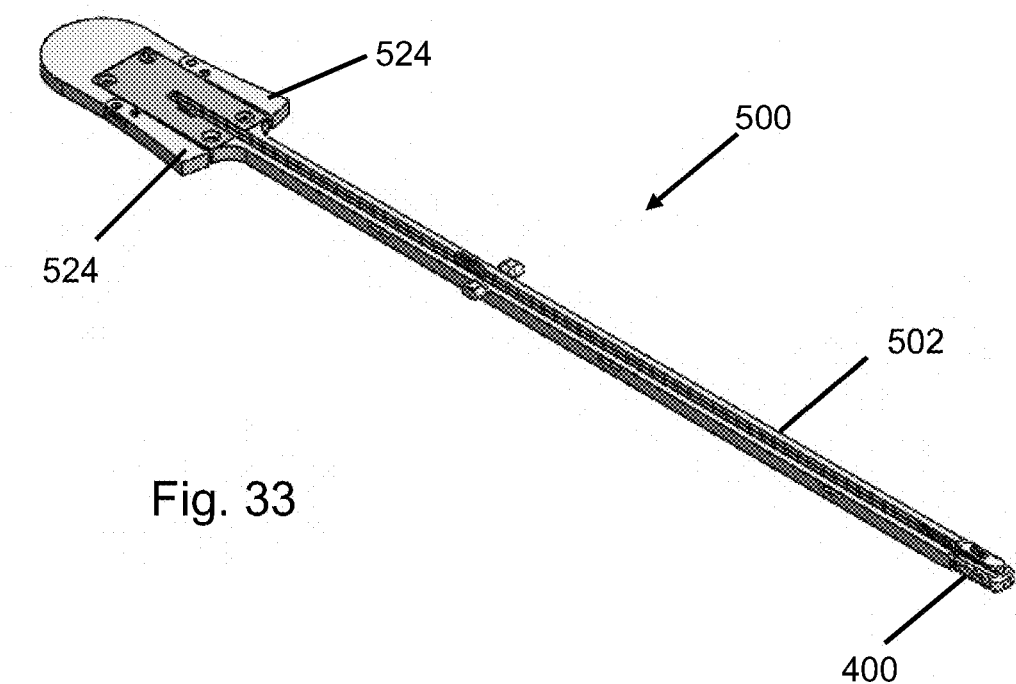
FIG. 33 is a perspective view of the surgical instrument with the semi-rigid surgical implant attached to the distal end thereof.
Figure 34:
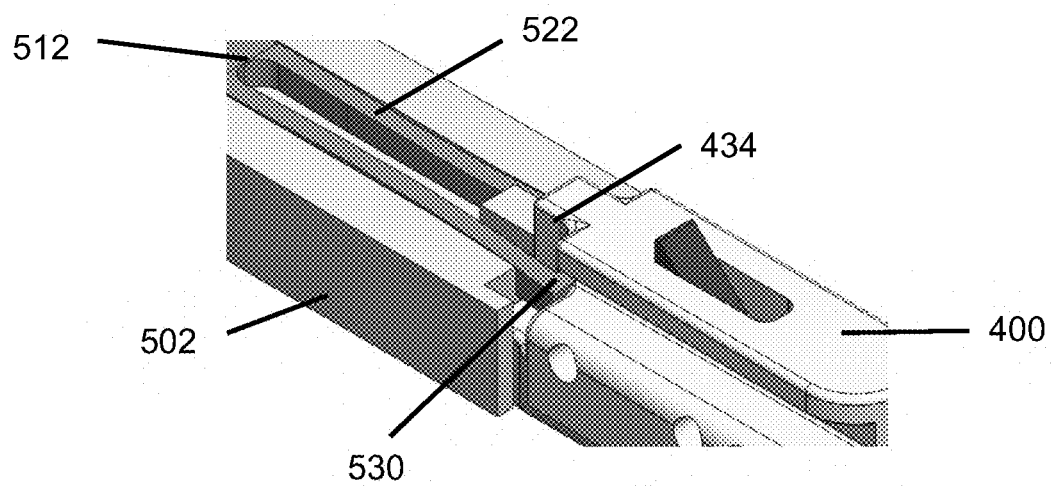
FIG. 34 is an enlarged perspective view of the distal end of the surgical instrument illustrated in FIG. 31 with the semi-rigid surgical implant attached thereto.
Figure 35:
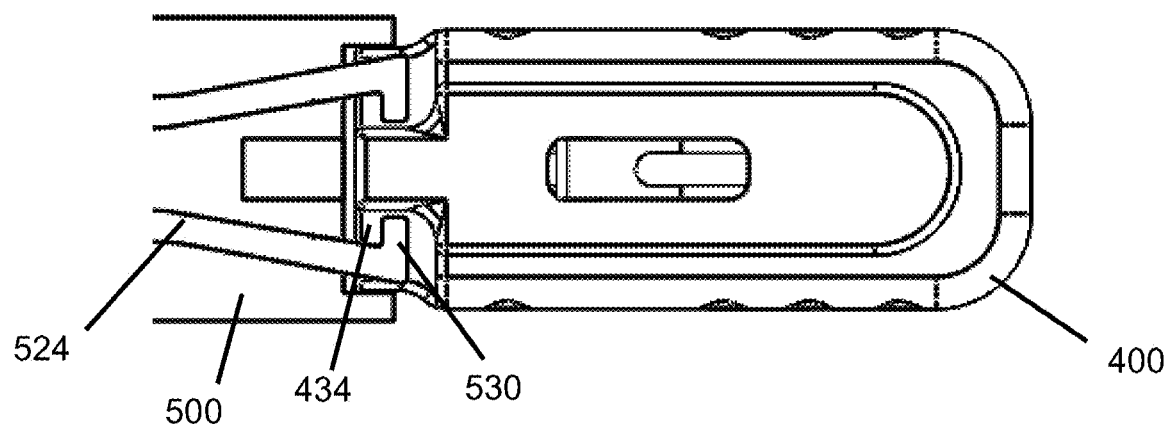
FIG. 35 is a top view of the semi-semi-rigid surgical implant engaged by the surgical instrument.

FIGS. 33-35 illustrate the arms 524 moved to the closed configuration and the inwardly directed tabs 530 engaging the tab regions 434 to secure the semi-rigid surgical implant 400 to the surgical implant inserter 500.

Figure 36:
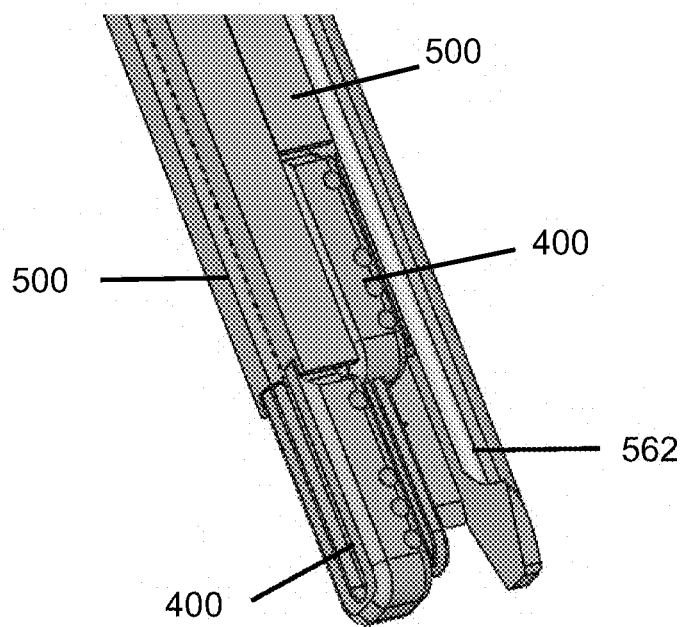
FIG. 36 is an enlarged perspective view of the semi-rigid surgical implant with an accessory shaft adapted as a distractor for sliding the two semi-rigid medical implants together.

FIG. 36 illustrates an accessory shaft 562 that extends from the surgical implant inserter 500. The accessory shaft 562 facilitates distracting or dilating bones or soft tissue to provide an opening into which the semi-rigid surgical implant 400 may be inserted.

Figure 37:
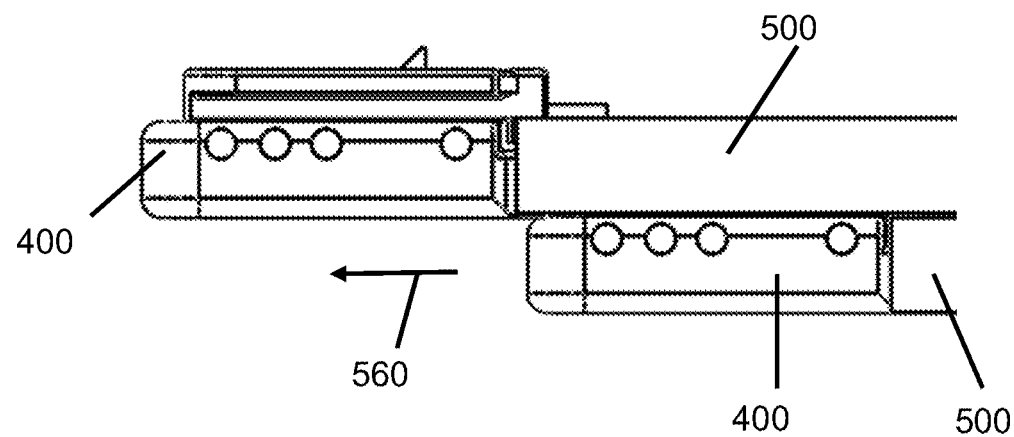
FIG. 37 is a side view of a second semi-rigid surgical implant that is engaged by a second surgical instrument being moved into engagement with a first semi-rigid surgical implant that is engaged by a second surgical instrument.

FIG. 37 illustrates two of the semi-rigid surgical implants 400 that are each attached to the surgical implant inserter 500 wherein the semi-rigid surgical implants 400 are sliding with respect to each other as indicated by arrow 560 during the process of slidably engaging the two semi-rigid surgical implants 400 to each other.

Figure 38:
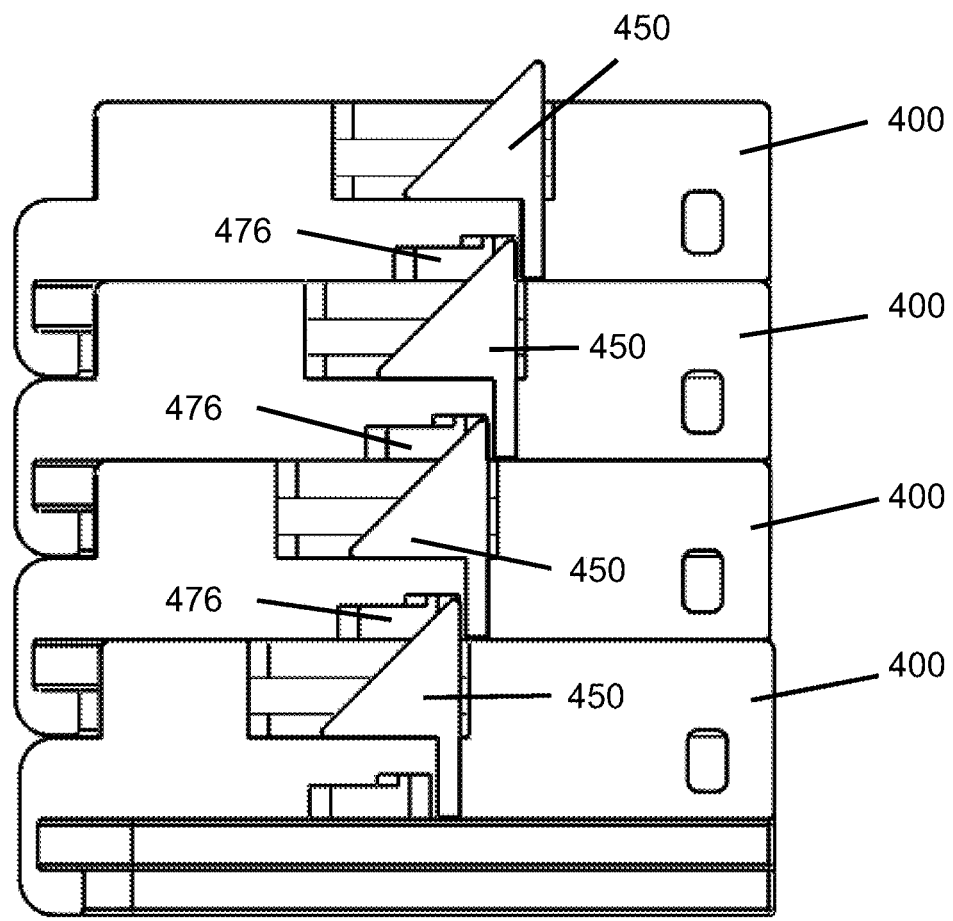
FIG. 38 is a side view of four of the semi-rigid medical implants in engagement with each other.

Once the two semi-rigid surgical implants 400 are aligned with each other, as illustrated in FIG. 38, the locking mechanism 450 extends into an opening 476 on the lower surface of the semi-rigid surgical implant 400 to prevent the two semi-rigid surgical implants 400 from sliding with respect to each other. While the locking mechanism 560 is deflectable to permit engagement of the two adjacent semi-rigid surgical implants 400, the locking mechanism 560 is not deflectable in a direction to permit detachment of the two adjacent semi-rigid surgical implants 400. This process is repeated until the combined thickness of the semi-rigid surgical implants 400 reaches a desired amount.

A person of skill in the art will appreciate that sensors or beacons appropriate for surgical navigation purposes may be placed on the surgical implant inserter 500 to aid in the use of the surgical implant inserter 500.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A semi-rigid surgical implant comprising:
an implant body having an opening formed therein, wherein the implant body is fabricated from a semi-rigid material;
a male engagement mechanism extending from an upper surface of the implant body;
a female engagement mechanism formed in a lower surface of the implant body, wherein a shape of the male engagement body is complementary to the female engagement body;
a locking mechanism seats at least partially in the opening, wherein the locking mechanism is deflectable from an undeflected configuration to a deflected configuration, wherein the locking mechanism comprises a main section having an aperture extending therethrough; and
a locking pin that extends through the aperture and the implant body to retain the locking mechanism in engagement with the implant body.

2. The semi-rigid surgical implant of claim 1, wherein the male engagement mechanism is engageable with a female engagement mechanism on a second semi-rigid surgical implant.

3. The semi-rigid surgical implant of claim 1, wherein the male engagement mechanism comprises:
a base engagement section attached to an upper surface of the implant body; and
an extension engagement section attached to the base engagement section opposite the implant body, wherein the extension engagement section has a width that is greater than a width of the base engagement section.

4. The semi-rigid surgical implant of claim 1, wherein the female engagement mechanism comprises:
a first channel section formed in a lower surface of the implant body; and
a second channel section formed in the implant body at an end of the first channel section that is opposite the lower surface of the first channel section, wherein the first channel section has a width that is greater than the second channel section.

5. The semi-rigid surgical implant of claim 4, wherein the implant body has a front surface and a back surface, wherein the first channel section and the second channel section are each closed at a first end thereof that is proximate the front surface and wherein the first channel section and the second channel section are each open at a second end thereof that is proximate the back surface.

6. The semi-rigid surgical implant of claim 1, wherein a portion of the locking mechanism extends above an upper surface of the implant body when the locking mechanism is in engagement with the implant body.

7. The semi-rigid surgical implant of claim 1, wherein the locking mechanism further comprises:
   at least one leg that extends from the main section, wherein the at least one leg is extendable into a mounting aperture in the implant body.

8. The semi-rigid surgical implant of claim 1, wherein at least a portion of the locking mechanism is fabricated from a flexible material.

9. The semi-rigid surgical implant of claim 1, wherein the main section has a triangular shape.

10. The semi-rigid surgical implant of claim 1, wherein the implant body further comprises a back surface and wherein a surgical instrument engagement region extends from the back surface.

11. The semi-rigid surgical implant of claim 1, wherein the implant body further comprises a side surface and wherein the implant body has at least one aperture formed in the side surface.

12. The semi-rigid surgical implant of claim 1, wherein the implant body has a durometer hardness of between about Shore 18A and about Shore 55D and wherein the implant body has a compressive modulus of between about 2 MPa and about 100 MPa.

13. The semi-rigid surgical implant of claim 1, wherein the aperture is wider proximate opposite ends thereof than intermediate the opposite ends of the aperture.

14. The semi-rigid surgical implant of claim 13, wherein the aperture is defined by a first line and a second line, wherein the first line and the second line intersect intermediate the opposite ends of the aperture and wherein the first line is oriented at an angle of between about 10 degrees and about 40 degrees.

15. A method of implanting a semi-rigid surgical implant comprising:
   providing a first semi-rigid surgical implant and a second semi-rigid surgical implant that each comprise an implant body, a male engagement mechanism, a female engagement mechanism, a locking mechanism and a locking pin, wherein the implant body has an opening formed therein, wherein the implant body is fabricated from a semi-rigid material, wherein the male engagement mechanism extends from an upper surface of the implant body, wherein the female engagement mechanism is formed in a lower surface of the implant body, wherein a shape of the male engagement body is complementary to the female engagement body, wherein the locking mechanism comprises a main section having an aperture extending therethrough, wherein the locking mechanism seats at least partially in the opening and wherein the locking pin extends through the aperture and the implant body to retain the locking mechanism in engagement with the implant body;
   sliding the first semi-rigid surgical implant with respect to the second semi-rigid surgical implant so that the male engagement mechanism on the first semi-rigid surgical implant extends into the female engagement mechanism on the second semi-rigid surgical implant;
   deflecting the locking mechanism from an undeflected configuration to a deflected configuration as the male engagement mechanism on the first semi-rigid surgical implant is extended into the female engagement mechanism on the second semi-rigid;
   wherein the locking mechanism returns to the undeflected configuration once the first semi-rigid surgical implant reaches an engaged position with respect to the second semi-rigid surgical implant; and
   wherein the locking mechanism once returned to the undeflected configuration retains the first semi-rigid surgical implant in the engaged position with respect to the second semi-rigid surgical implant.

16. The method of claim 15, and further comprising:
   providing a surgical instrument comprising a shaft, an accessory shaft, an actuation mechanism and an implant engagement mechanism, wherein the shaft has a channel formed therein, wherein the shaft has a proximal end and a distal end, wherein the accessory shaft is slidably mounted in the channel, wherein the accessory shaft has a proximal end and a distal end, wherein the actuation mechanism is mounted to the shaft proximate the proximal end thereof and wherein the implant engagement mechanism is attached to the distal end of the accessory shaft;
   positioning the first semi-rigid surgical implant proximate the implant engagement mechanism;
   using the actuation mechanism to cause the accessory shaft to slide with respect to the shaft and cause the implant engagement mechanism to engage the first semi-rigid surgical implant;
   manipulating the surgical instrument to position the semi-rigid surgical instrument at least partially between a first bone and a second bone; and
   using the actuation mechanism to cause the accessory shaft to slide with respect to the shaft and cause the implant engagement mechanism to disengage the first semi-rigid surgical implant.

17. The method of claim 15, wherein the locking mechanism further comprises at least one leg that at least one leg extends from the main section, wherein the at least one leg extends into a mounting aperture in the implant body and wherein the aperture permits the main section to pivot from the undeflected configuration the deflected configuration with the locking pin extending through the aperture.

18. The method of claim 17, wherein at least a portion of the locking mechanism is fabricated from a flexible material and wherein the main section has a triangular shape.

* * * * *